(12) United States Patent
Moore et al.

(10) Patent No.: US 11,383,102 B2
(45) Date of Patent: Jul. 12, 2022

(54) THREE-DIMENSIONAL RADIOTHERAPY DOSE DISTRIBUTION PREDICTION

(71) Applicant: The Regents of the University of California, Oakland, CA (US)

(72) Inventors: Kevin Moore, San Diego, CA (US); Satomi Shiraishi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/080,681

(22) Filed: Oct. 26, 2020

(65) Prior Publication Data
US 2021/0085997 A1 Mar. 25, 2021

Related U.S. Application Data

(63) Continuation of application No. 15/528,734, filed as application No. PCT/US2015/062013 on Nov. 20, 2015, now Pat. No. 10,850,121.

(60) Provisional application No. 62/184,141, filed on Jun. 24, 2015, provisional application No. 62/082,860, filed on Nov. 21, 2014.

(51) Int. Cl.
*A61N 5/10* (2006.01)
*G16H 50/50* (2018.01)
*G16H 20/40* (2018.01)
*G16Z 99/00* (2019.01)

(52) U.S. Cl.
CPC .......... *A61N 5/1031* (2013.01); *G16H 20/40* (2018.01); *G16H 50/50* (2018.01); *G16Z 99/00* (2019.02); *A61N 2005/1041* (2013.01)

(58) Field of Classification Search
None
See application file for complete search history.

(56) References Cited

U.S. PATENT DOCUMENTS

2012/0310615 A1* 12/2012 Moore ................ A61N 5/1031
703/11
2017/0340900 A1 11/2017 Moore et al.

OTHER PUBLICATIONS

Cochocki A, Unbehauen R. *Neural networks for optimization and signal processing*: John Wiley & Sons, Inc.; 1993.
Haykin SS. *Neural networks and learning machines*. vol 3: Pearson Education Upper Saddle River; 2009.
Michalski, J. M. H. Gay, A. Jackson, S. L. Iluker, and .1. O. Deasy, "Radiation Dose-Volume Effects in Radiation-Induced Rectal Injury," Int J Radiat Oncol Biol Phys 76, 123-9 (2010).
Mundt AJ, Yashar C, Mell LK. *Gynecologic Cancer*. vol 2: Demos Medical Publishing; 2011.
Oh K-S, Jung K. GPU implementation of neural networks. *Pattern Recognition*. 2004;37(6):1311-1314.

(Continued)

*Primary Examiner* — Hoon K Song
(74) *Attorney, Agent, or Firm* — Mintz Levin Cohn Ferris Glovsky and Popeo, P.C.

(57) ABSTRACT

Generating a three-dimensional radiation dose matrix for a patient for controlling the delivery of radiation dose to patients. The three-dimensional radiation dose matrix for the patient based on an intensity of radiation fields delivered by a radiation therapy delivery system that intersect with volume elements of a patient and determined by a predictive model. The intensity of the radiation fields at volume elements of the patient determined from spatial position data of the volume elements in a patient and radiation therapy delivery system data.

22 Claims, 18 Drawing Sheets

(56) References Cited

OTHER PUBLICATIONS

Otto K. Real-time interactive treatment planning. *Physics in medicine and biology*. 2014;59(17):4845.
Pan H, Cerviño Li, Pawlicki T, et al. Frameless, real-time, surface imaging-guided radiosurgery: clinical outcomes for brain metastases. *Neurosurgery*. 2012;71(4):844-852.
Papp D, Unkelbach J. Direct leaf trajectory optimization for volumetric modulated arc therapy planning with sliding window delivery. *Medical physics*. 2014;41(1):011701.
Peng F, Jia X, Gu X, Epelman MA, Romeijn HE, Jiang SB. A new column-generation-based algorithm for VMAT treatment plan optimization. *Physics in medicine and biology*. 2012;57(14):4569.
Peters LJ, O'Sullivan B, Giralt J, et al. Critical impact of radiotherapy protocol compliance and quality in the treatment of advanced head and neck cancer: results from TROG 02.02. *Journal of clinical oncology*. 2010;28(18):2996-3001.
Quan EM, Chang JY, Liao Z, et al. Automated Volumetric Modulated Arc Therapy Treatment Planning for Stage III Lung Cancer: How Does It Compare With Intensity-Modulated Radio Therapy? *International Journal of Radiation Oncology\*Biology\*Physics*. Sep. 1, 2012;84(1):e69-e76.
Reft C, Alecu R, Das IJ, et al. Dosimetric considerations for patients with HIP prostheses undergoing pelvic irradiation. Report of the AAPM Radiation Therapy Committee Task Group 63. *Medical physics*. 2003:30(6):1162-1182.
Schreibmann E, Dhabaan A, Elder E, Fox T. Patient-specific quality assurance method for VMAT treatment delivery. *Medical physics*. 2009;36(10):4530-4535.
Shiraishi S, Tan J, Olsen LA, Moore KL. Knowledge-based prediction of plan quality metrics in intracranial stereotactic radiosurgery. *Medical Physics*. 2015;42(2):908-917.
Siochi RA, Balter P, Bloch CD, et al. A rapid communication from the AAPM Task Group 201: recommendations for the QA of external beam radiotherapy data transfer. AAPM TG 201: quality assurance of external beam radiotherapy data transfer. *J Appl Clin Med Phys*. 2011;12(1):3479.
Sun B, Song J, Zhu G, Shi L. A two-stage approach for VMAT treatment plan optimization. Paper presented at: Automation Science and Engineering (CASE), 2013 IEEE International Conference on2013.
Sutcliffe KM, Lewton E, Rosenthal MM. Communication failures: an insidious contributor to medical mishaps. *Academic Medicine*. 2004;79(2):186-194.
Voet PW, Dirkx ML, Breedveld S, Fransen D, Levendag PC, Heijmen BJ. Toward Fully Automated Multicriterial Plan Generation: A Prospective Clinical Study. *Int J Radial Oncol Biol Phys*. Jun. 2012.
Wu B, McNutt T, Zahurak M, et al. Fully Automated Simultaneous Integrated Boosted-Intensity Modulated Radiation Therapy Treatment Planning is Feasible for Head-and-Neck Cancer: A Prospective Clinical Study. *International Journal of Radiation Oncology\* Biology\* Physics*. 2012.
Wu B, Ricchetti F, Sanguineti G, et al. Data-Driven Approach to Generating Achievable Dose-Volume Histogram Objectives in Intensity-Modulated Radiotherapy Planning. *International Journal of Radiation Oncology\*Biology\*Physics*. Mar. 15, 2011;79(4):1241-1247.
Wu, B. D. Pang, S. Lei, J. Gatti, M. Tong, T. McNutt, T. Kole, A. Dritschilo, and S. Collins, "Improved robotic stereotactic body radiation therapy plan quality and planning efficacy for organ-confined prostate cancer utilizing overlap-volume histogram-driven planning methodol-ogy," Radiother Oncol 112, 221-6 (2014).
Yan D. Adaptive radiotherapy: merging principle into clinical practice. Paper presented at: Seminars in radiation oncology2010.
Yang D, Moore KL. Automated radiotherapy treatment plan integrity verification. *Med Phys*. Mar. 2012;39(3):1542-1551.
Zhu X, Ge Y, Li T, Thongphiew D, Yin FF, Wu QJ. A planning quality evaluation tool for prostate adaptive IMRT based on machine learning. *Med Phys*. Feb. 2011;38(2):719-726.

\* cited by examiner

302

304

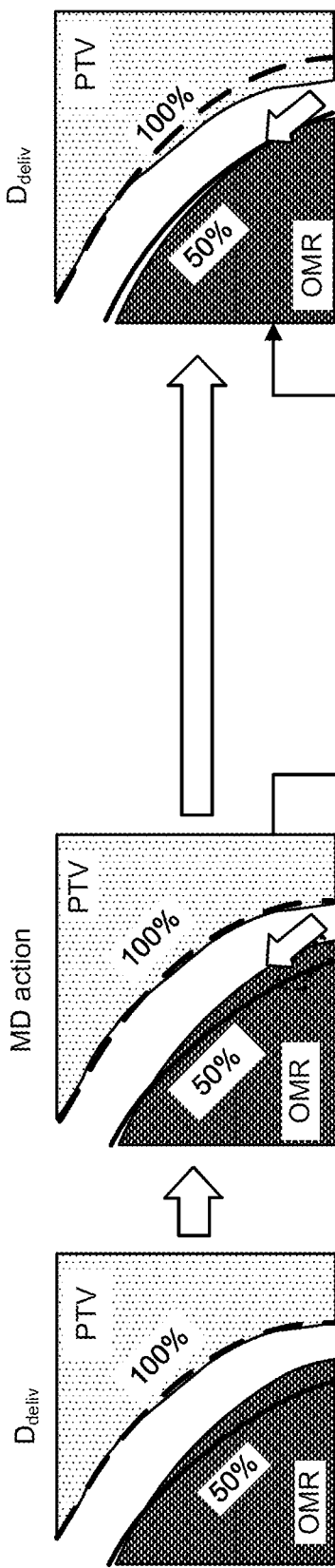

THREE-DIMENSIONAL RADIOTHERAPY DOSE DISTRIBUTION PREDICTION

CROSS-REFERENCE TO RELATED APPLICATIONS

This application is a continuation application of U.S. patent application Ser. No. 15/528,734 filed May 22, 2017, entitled "THREE-DIMENSIONAL RADIOTHERAPY DOSE DISTRIBUTION PREDICTION," which is a national-phase entry of Patent Cooperation Treaty Application No. PCT/US2015/062013, which has an international filing date of Nov. 20, 2015, entitled "THREE-DIMENSIONAL RADIOTHERAPY DOSE DISTRIBUTION PREDICTION," which claims the benefit of and priority to U.S. Provisional Patent Application No. 62/082,860, filed on Nov. 21, 2014, entitled "THREE-DIMENSIONAL RADIOTHERAPY DOSE DISTRIBUTION PREDICTION," and U.S. Provisional Patent Application No. 62/184,141, filed on Jun. 24, 2015, entitled "THREE-DIMENSIONAL RADIOTHERAPY DOSE DISTRIBUTION PREDICTION," the entire contents of these applications are incorporated herein by reference in their entirety.

TECHNICAL FIELD

The subject matter disclosed herein relates to radiotherapy dose distribution prediction.

BACKGROUND

Radiation therapy, or radiotherapy, is therapy using ionizing radiation. Radiotherapy is typically administered as part of cancer treatment to control or kill malignant cells. Radiation therapy can be curative in the treatment of some types of cancer when localized to the parts of the body that contain cancer cells. Radiation therapy may also be used to prevent tumor recurrence after surgery to remove a primary tumor.

Radiation therapy works by the ionizing radiation damaging the DNA of cancerous tissue leading to cellular death. Ionizing radiation can include charged massive particles that can ionize atoms directly through fundamental interactions with the atoms. Such particles can include atomic nuclei, electrons. Photons, charges ions, protons, and energetic charge nuclei stripped of their electrons. Photons can also ionize atoms directly through the photoelectric effect and the Compton Effect Photons typically cause an atom to eject an electron at relativistic speeds, turning the electron into a beta particle which goes on to ionize many other atoms.

Ionizing radiation can damage the DNA of healthy tissue just as it does cancerous tissue. There are a number of techniques that are employed to reduce the likelihood of destroying healthy tissue that is in the path of the ionizing radiation. One such method is to provide shaped radiation beams. The radiation beams can be shaped to mimic the cross-section of a tumor. This minimizes the amount of healthy tissue that the radiation beam intersects. Other techniques include aiming multiple radiation beams, or shaped radiation beams, from different angles around the patient, such that each beam travels through a different path in the patient to reach the tumor. The radiation beams typically intersect within the boundaries of the tumor, thereby delivering a much greater dose of radiation to the cancerous cells, compared to the health tissue surrounding the tumor. Margins are typically provided to account for uncertainties in the location of the tumor caused by patient movement during treatment, equipment set-up variations, and the like.

Imaging systems, such as computerized tomography (CT) scanners, and magnetic resonance imaging (MRI), can be used to delineate tumors and adjacent healthy structures in three-dimensions. Virtual simulation based on the three-dimensional images of the patient, can allow for increased accuracy of the placement of radiation beams compared to systems relying on more conventional imaging systems.

Three-dimensional conformal radiation therapy (3DCRT) can be used, in which the profile of each radiation beam is shaped to conform to the profile of the tumor, or treatment target of the patient, from a beam's eye view. Shape confirmation can be achieved using a multileaf collimator. A variable number of beams can also be used to more accurately fit the shape of the tumor. Conforming the radiation therapy beams to the shape of the tumor reduces the radiation toxicity to surrounding tissue. Consequently, the dose of radiation provided to the tumor can be increased.

Intensity-modulated radiation therapy (IMRT) can tailor the strength of the radiation delivered to various parts of the tumor. This is especially effective when a tumor surrounds an important bodily structure, such as the spinal cord. IMRT is typically performed with the use of computer-controlled x-ray accelerators distributing precise radiation doses across the tumor. The radiation dose intensity can be controlled, or modulated to make the radiation dose consistent with the three-dimensional shape of the tumor. The radiation dose intensity can be elevated near the gross tumor volume, while decreased around the neighboring tissue.

Volumetric modulated are therapy (VMAT) can achieve highly conformal dose distributions on the treatment target, sparing normal tissue. VMAT can use a rotating gantry to deliver radiation therapy, changing the shape and speed of the radiation beam as well as the dose rate.

Other types of radiation therapy include particle therapy, auger therapy, brachytherapy, and the like.

Various treatment planning optimization techniques exist for developing radiation dose patterns, or fluence patterns, for external beam radiation therapy treatment plans. As previously stated, treatment planning can include obtaining images of the patient using CT and MRI technologies. The CT and MRI measurements can be used to determine the location of the treatment target of the patient as well as surrounding tissues that are at risk from being irradiated. Organs surrounding the treatment target, or in the path of the radiation beams, can be called "Organs-at-Risk" (OARs). The area of the patient to which the radiation is intended to be provided can be called the planning treatment target (PTV). OARs and the PTV can have complex three-dimensional shapes that make preparing the radiotherapy treatment plan a complex task.

Various computing systems have been developed to facilitate preparation of a treatment plan for patients. Typically, the treatment planning systems are configured to import three-dimensional images from one or more diagnostic imaging sources, such as CT scanners, MRI machines, or the like. The resultant "volume" may then be split into multiple different volume elements, or "voxels." A dosage amount for each volume element can then be determined.

During radiotherapy planning, volumetric elements are delineated to be targeted or avoided with respect to the administration of a radiation dose, Once the PTV has been defined, and the OARs have been identified, a responsible radiation oncologist can specify a desired radiation dose to the PTV and the allowable dose to OARs. The planning software can then produce a treatment plan that attempts to meet the clinical dosimetric objectives. The treatment plan is the programmed set of instructions to the radiation delivery machine, but can be summarized for its clinical effect on the patient in terms of dose-volume relationships that can include a three-dimensional dose matrix. One commonly used embodiment of a dose-volume relationship is the dose-volume histogram (DVH) that summarizes the frequency distribution of radiation doses in a particular PTV or OAR structure.

The presently available treatment planning computing systems require highly subjective input by numerous medical professionals and rely on their level of expertise, biases, and the amount of time the medical professional is able to dedicate to the treatment plan. This can lead to the unnecessary irradiation of OARs or a missed opportunity to provide higher intensity doses to the PTV.

SUMMARY

In one aspect methods and systems and non-transitory computer program product are described. The method can include one or more operations to be performed by at least one data processor forming at least part of a computing system. The system can include at least one data processor and at least one memory coupled to the at least one data processor. The at least one memory can be configured to store instructions, which, when executed, can cause the at least one data processor to perform one or more operations. The non-transitory computer program product can include instructions, that when executed by at least one programmable processor, forming at least part of a computing system, can cause the at least one programmable processor to perform one or more operations.

The one or more operations can include selecting data corresponding to the spatial position of one or more volume elements of a target patient. Data can be selected that corresponds to a set-up of a radiation therapy delivery system for delivering one or more radiation fields to the patient. A determination can be triggered to determine an intensity of radiation fields delivered by the radiation therapy delivery system. The intensity of the radiation fields can be determined for radiation fields that intersect with individual volume elements of the one or more volume elements of the patient. The intensity at the volume elements can be determined. A three-dimensional radiation dose matrix can be generated for the patient. The three-dimensional radiation dose matrix can be generated based on a predictive model.

In some variations, the one or more operations can include generating a radiation therapy treatment plan for the patient based on the three-dimensional radiation dose matrix for the patient. The three-dimensional radiation dose matrix can include a quantity of radiation provided to the one or more volume elements of the patient. Data corresponding to one or more radiation therapy clinical objectives can be received and the generating of a radiation therapy treatment plan for the patient can be based on the data corresponding to the or more radiation therapy clinical objectives. A radiation therapy treatment plan can be generated for the patient based on their unique anatomical structure.

In some variations, a graphical user interface can be generated for presentation on a screen of a user device. The user device can be associated with a medical practitioner displaying the generated radiation therapy treatment plan for the patient.

In some variations, modifications to the generated radiation therapy treatment plan for the patient can be facilitated. In some variations, modification can be performed via the graphical user interface.

In some variations, the predictive model can be trained using a machine learning system.

In some variations, the at least one data processor can be included in circuitry that is part of a radiation dose system.

In some variations, the three-dimensional radiation dose matrix for the patient can be based on the quantity of radiation fields that intersect with the one or more volume elements of the patient. Basing the three-dimensional radiation dose matrix for the patient on the quantity of radiation fields that intersect with the one or more volume elements of the patient can includes selecting, for individual ones of the one or more volume elements of the patient, a maximum radiation dose. A three-dimensional radiation dose matrix can be determined for the patient where the radiation dose experienced for individual ones of the one or more volume elements is less than or equal to the selected maximum radiation dose.

In some variations, the data corresponding to the spatial position of the one or more volume elements of the patient can include the spatial position of the one or more volume elements with respect to an organ structure(s) of the patient, a treatment target(s) of the patient, an anatomical structure(s) of the patient, or the like.

In some variations, the spatial position of the one or more volume elements with respect to the treatment target of the patient can include a distance of the one or more volume elements from an organ structure(s) of the patient, a treatment target(s) of the patient, an anatomical structure(s) of the patient, or the like.

In some variations, the spatial position of the one or more volume elements with respect to the treatment target of the patient can include an orientation of the one or more volume elements with respect to an organ structure(s) of the patient, a treatment target(s) of the patient, an anatomical structure(s) of the patient, or the like.

In some variations, the data corresponding to the spatial position of one or more volume elements of a patient can include a matrix of a plurality of volume elements in the vicinity of the treatment target of the patient. The data corresponding to the spatial position of one or more volume elements of a patient can include angular parameters of one or more volume elements of the patient.

In some variations, the data corresponding to a set-up of a radiation therapy delivery system for delivering one or more radiation fields to the patient can include a field angle(s), a field strength(s), a field aperture(s), or the like, of the field(s) delivered to the patient.

The data corresponding to a set-up of a radiation therapy delivery system for delivering one or more radiation fields to the patient can include a position of a couch with respect to one or more elements of the radiation therapy delivery system.

In some variations, the machine learning system is a neural network.

In some variations, the three-dimensional radiation dose matrix can include a radiation dose to the one or more volume elements of the patient.

In some variations, the radiation fields can include photon beams, ion beams, other radiation beams, or the like.

In some variations, the determination of the quantity of radiation fields delivered by the radiation therapy delivery system that will intersect with individual volume elements of the one or more volume elements of the patient can be limited to the one or more volume elements outside of the treatment target of the patient, to one or more volume elements within the treatment target of the patient, or the like.

In some variations, the predictive model can be based on a plurality of reports that include observed radiation field patterns in one or more volume elements of prior patients.

In some variations, the one or more volume elements are one or more voxels.

In another aspect, a means for generating a radiation dose matrix for a patient is described. The means for generating a radiation dose matrix for a patient can use a predictive model. The radiation dose matrix for the patient can be based on a spatial position of one or more volume elements of a target patient. The radiation dose matrix for the patient can be based on a set-up of a radiation therapy delivery system for delivering one or more radiation fields to the patient. The means for generating a radiation dose matrix for a patient can be configured to perform one or more of the operations described herein.

Implementations of the current subject matter can include, but are not limited to, systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, show certain aspects of the subject matter disclosed herein and, together with the description, help explain some of the principles associated with the disclosed implementations. In the drawings.

FIG. 15B depicts another example of a GUI consistent with the current subject matter;

FIG. 15C depicts another example of a GUI consistent with the current subject matter;

FIG. 15D depicts another example of a GUI consistent with the current subject matter;

FIG. 15E depicts another example of a GUI consistent with the current subject matter;

FIG. 15F depicts another example of a GUI consistent with the current subject matter.

DETAILED DESCRIPTION

Figure 1:
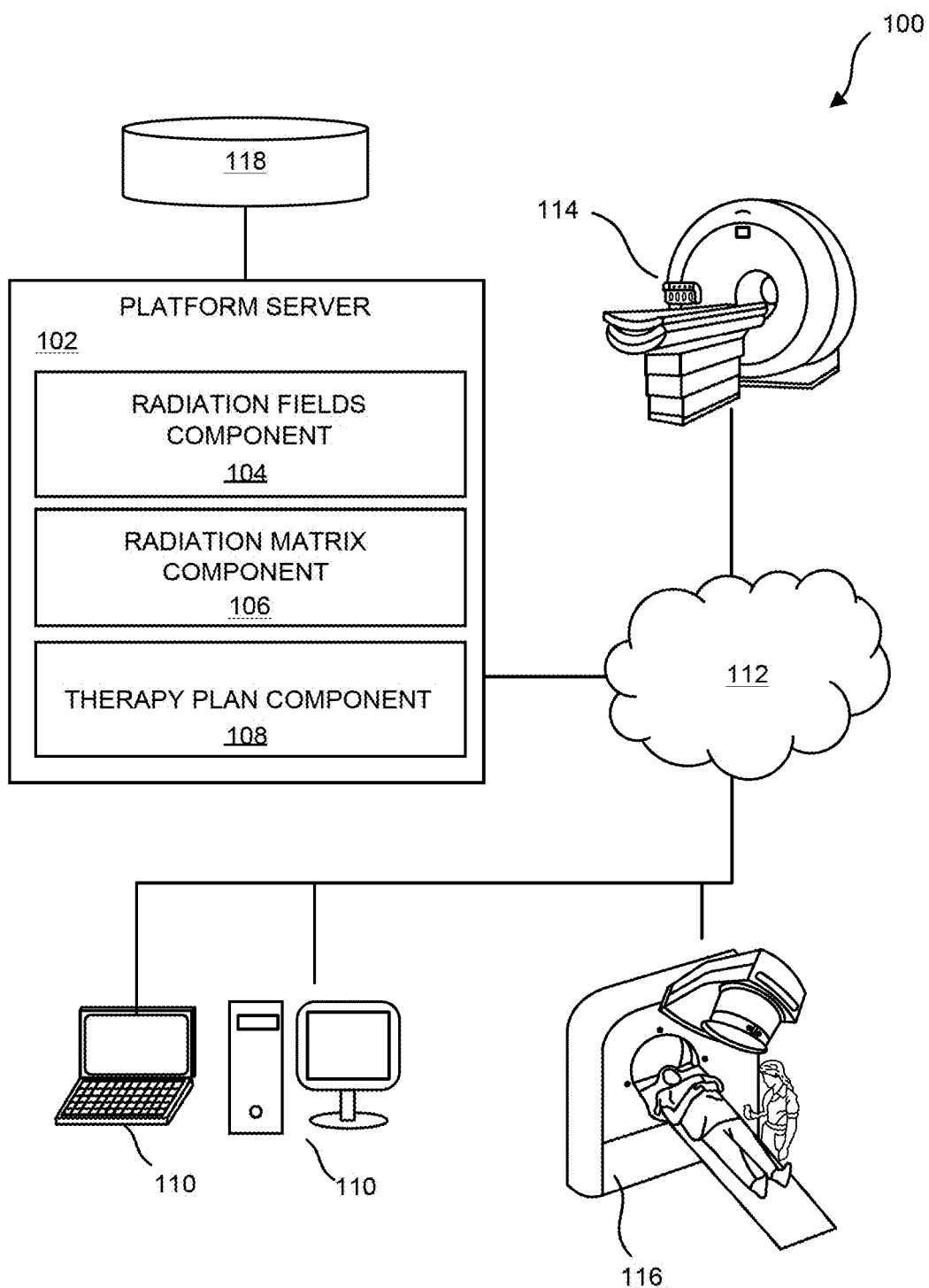
FIG. 1 is a diagram of a system having one or more elements consistent with the current subject matter.

The presently available treatment planning computing systems require highly subjective input by numerous medical professionals and rely on their level of expertise, biases, and the amount of time the medical professional is able to dedicate to the treatment plan. This can lead to the unnecessary irradiation of OARs or a missed opportunity to provide higher intensity doses to the PTV. Ultimately, plan quality deficiencies can put a significant proportion of patients who should have a low risk of radiation-induced complications at much higher risk for poor outcome.

While knowledge-based planning (KBP) computing systems can offer a means to eliminate poor quality treatment planning, existing KBP methods still rely on dose-volume histogram (DVH) prediction at their core. Reliance on DVH-based plan optimizers precludes the treatment design process from being driven by a patient's radiation oncologist.

The presently described subject matter provides computing systems capable of providing highly accurate predictions using three-dimensional distributions. The computing systems can be configured to synthesize anatomy-to-dose correlations from previously treated patients. The synthesis can be performed on a volume-element-by-volume-element basis. This allows the radiation oncologist to see a highly accurate representation of an achievable final dose distribution immediately after completion of normal tissue and tumor contouring.

In some variations, the synthesis can be performed on a voxel-by-voxel basis. A voxel being a volume-element which may be characterized as a rectangular object of width, height, and depth corresponding to the resolution of the cardinal axes in a three-dimensional medical image. A voxel may also be characterized by its size in each dimension and its location in space. Consequently, the term voxel may refer to a dynamically changing volume depending on how the operator controls the computing system.

The presently described subject matter contemplates using the knowledge-based three-dimensional dose prediction to facilitate physician-driven isodose adjustment by a radiation oncologist, or the like, according to a patient's unique clinical circumstances.

The subject matter disclosed herein can, in some example embodiments, synthesize information from previously treated radiotherapy patients into a system that can make predictions for what radiotherapy dose distributions will look like in three-dimensions for new treatment plans for patients based on their unique anatomical features. This can allow clinicians to know what radiotherapy will do for a particular patient, without incurring the time and effort of the planning process, as well as facilitating both automated treatment planning, optimization methods, and treatment plan quality control.

In some example embodiments, a correlation can be drawn between geometric parameters of the patient anatomy and the value of observed radiation dose distributions for clinically treated plans. Geometric parameters of the patient's anatomy can include, for example, the position and orientation of PTV volume-elements, OAR volume elements, with respect to one or more locations within the patient or the radiation treatment system.

Previous systems have focused almost exclusively on distance correlations that yielded dose volume histogram predictions. Fundamentally, these system do not have the ability to describe exactly where the radiation dose was being deposited in orientation. The subject matter described herein can incorporate angular parameters and further treatment geometric information to allow not just a distance-dose correlation but a dose-angular correlation as well. Such treatment geometric information can include beam strengths, beam widths, beam shapes, beam orientations, or the like. With the ability to predict how the dose changes with both distance and angular orientation from the tumorous target boundary, the system described herein can create an expected three-dimensional dose distribution for new patients.

FIG. 1 is a diagram of a system 100 having one or more elements consistent with the current subject matter. The system 100 can comprise a computing system such as a platform server 102. The platform server 102 can include a personal computing system, a server located at a treatment facility, a server located at a remote location to the treatment facility, or the like. The platform server 102 can be configured to perform one or more operations, such as the operations described herein. The operations can be performed by one or more components, for example, the radiation fields component 104, radiation matrix component 106, a therapy plan component 108, or the like. The platform server 102 can include one or more processors configured to cause the platform server 102 to perform one or more operations defined by components 104, 106, 108, or the like.

Although FIG. 1 illustrates components 104, 106 and 108 as separate components, the functionality provided or facilitated by components 104, 106 and 108 can be performed by a single component, a combination of components, one or more other components, or the like. System 100 is an exemplary illustration only and is not intended to provide any limitations.

In some variations, the platform server 102 can be configured to communicate with one or more user devices 110. The platform server 102 may be configured to communicate with the one or more devices directly or through a communication network 112. The communication network 112 can be a local area network, wide area network, or other network type.

The system 100 can include one or more imaging devices 114. The one or more imaging devices 114 can include a CT machine, MRI machine, X-ray machine, or the like. Measurement data obtained by the one or more imaging devices 114 can be obtained by the platform server 102. The measurement data can be assimilated by the platform server 102. In some variations, the measurement data can be assimilated by the one or more imaging devices 114.

The system 100 can include one or more radiation therapy systems 116. The radiation therapy systems 116 can be configured to implement a radiation therapy plan generated by the platform server 102. The radiation therapy plan can be transmitted to the one or more radiation therapy systems 116.

The system 100 can include one or more electronic storage devices 118. The electronic storage device(s) 118 can be associated with the platform server 102. The electronic storage device(s) 118 can be associated with a data center remote from the platform server 102. The electronic storage device(s) 118 can store historical information related to radiation therapy patients.

Figure 2:
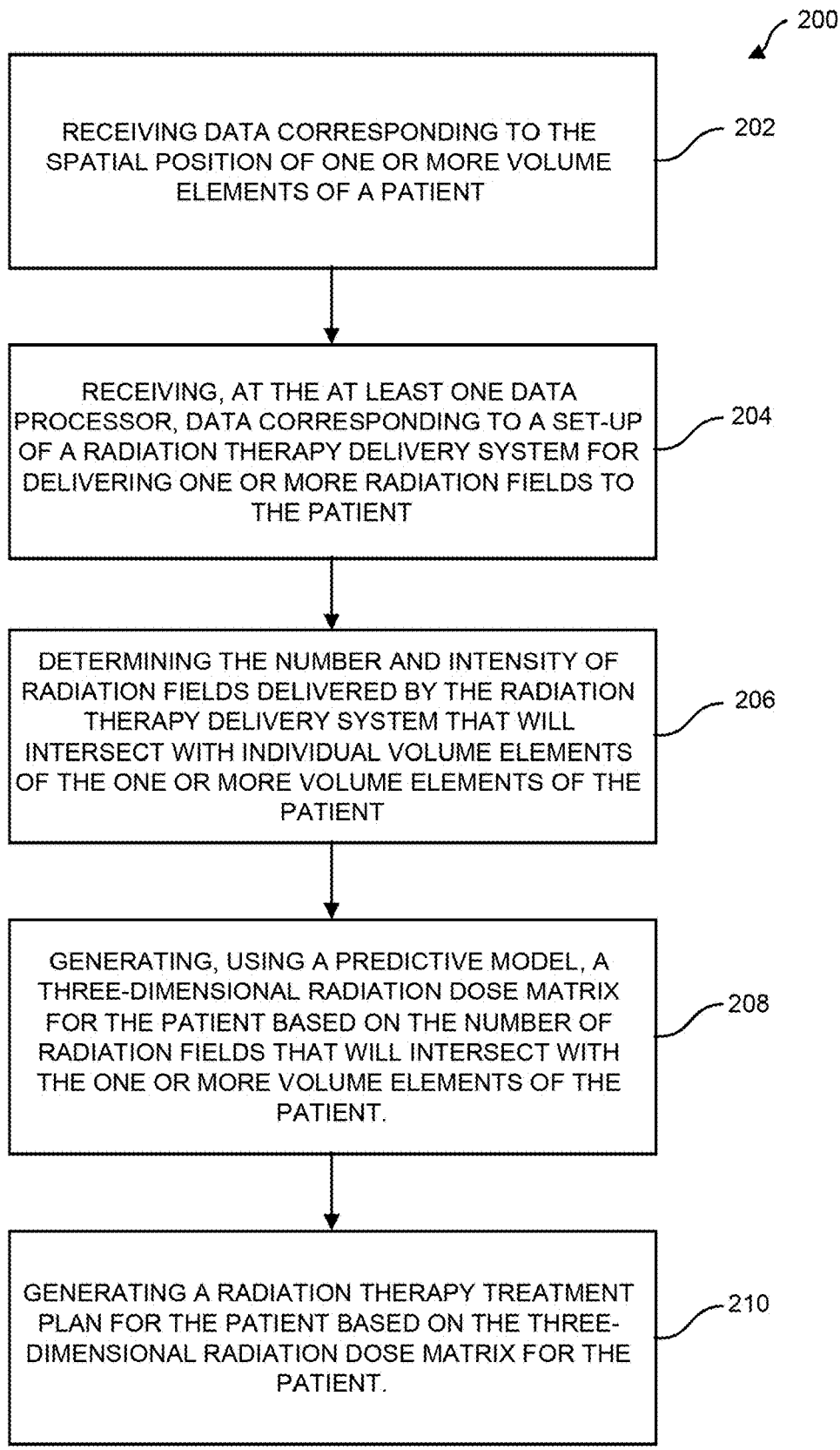
FIG. 2 is an illustration of an example process by which an expected three-dimensional radiotherapy dose distribution can be generated for new patients, the process having one or more elements consistent with the current subject matter.

FIG. 2 is an illustration of an example process 200 by which an expected three-dimensional radiotherapy dose distribution can be generated for new patients, the process having one or more elements consistent with the current subject matter. One or more of the operations described in relation to process 200 may be performed by one or more components of system 100.

At 202, data can be received that corresponds to the spatial position of one or more volume elements of a patient. In some variations, the data can be received by at the platform server 102.

In some variations, the data corresponding to the spatial position of the one or more volume elements of the patient can include the spatial position of the one or more volume elements with respect to organ structures of the patient, OARs, the PTV(s), or the like. In some variations, the spatial position of the one or more volume elements with respect to the treatment target of the patient includes a distance of the one or more volume elements from an edge of the treatment target of the patient, an orientation of the one or more volume elements with respect to a surface of the treatment target of the patient, or the like.

The spatial position of one or more volume elements of a patient can be provided as a matrix of a plurality of volume elements in the vicinity of the treatment target of the patient. The volume elements can be obtained from an analysis of CT, MRI, X-ray, measurements of the patient, or the like. These can be referred to as three-dimensional imagery data. The three-dimensional imagery data can be used to distinguish between OARs and PTVs and other boundaries within the patient. In some variations, the three-dimensional imagery data can store the information as a set of volume elements. These volume elements may be stored as voxels within the three-dimensional imagery data.

Figure 3A:
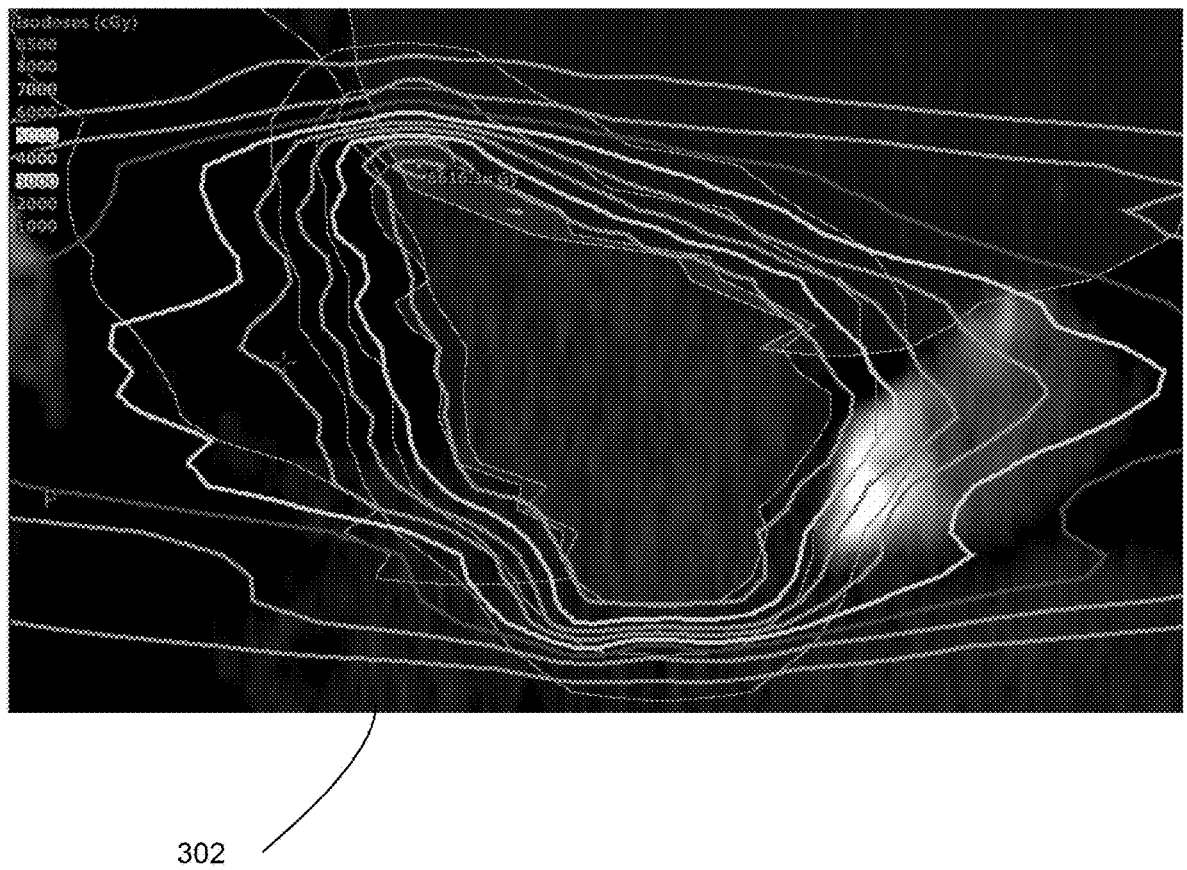
FIG. 3A is an illustration of an example of a voxel that share a range of boundary distances, forming a shell around the PTV in three planes of the patient, the illustration obtained by one or more elements consistent with the current subject matter.
Figure 3B:
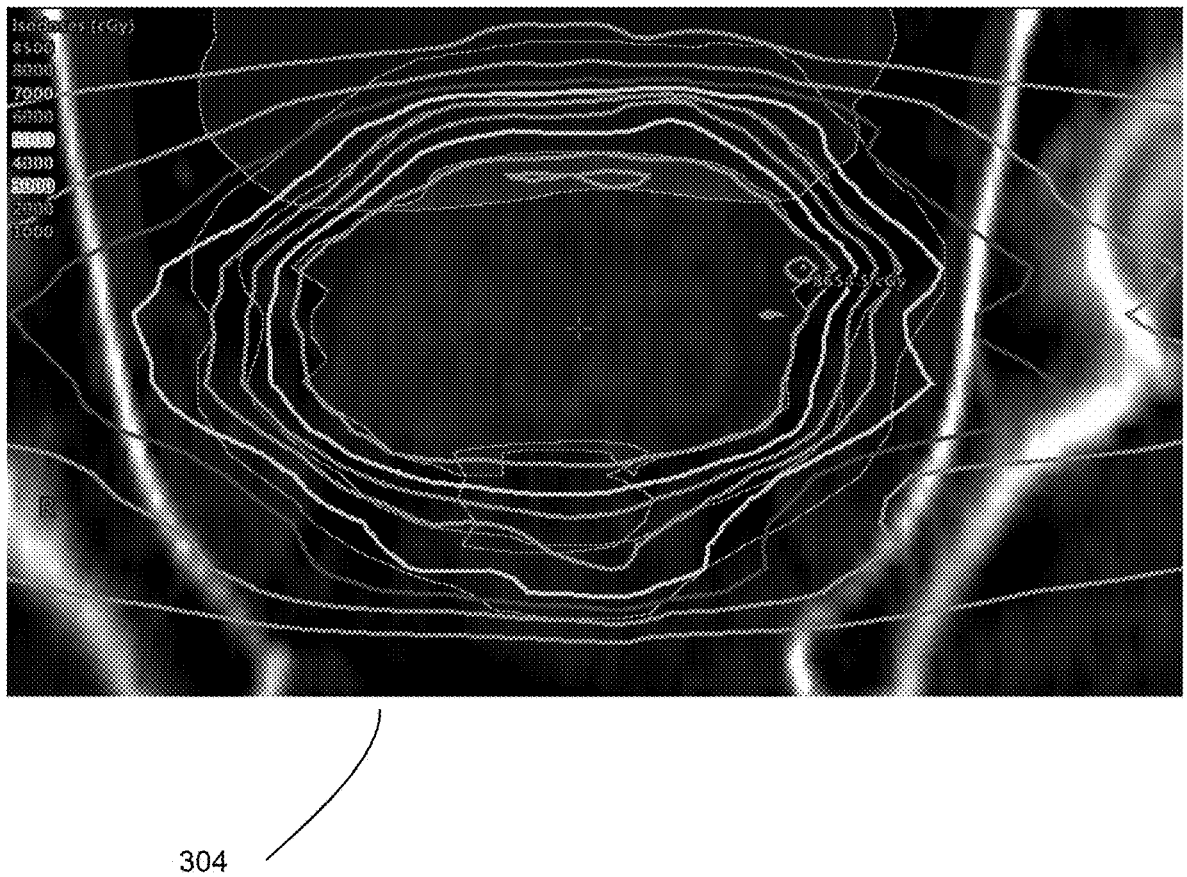
FIG. 3B is an illustration of another example of a voxel that share a range of boundary distances, forming a shell around the PTV in three planes of the patient, the illustration obtained by one or more elements consistent with the current subject matter.
Figure 3C:
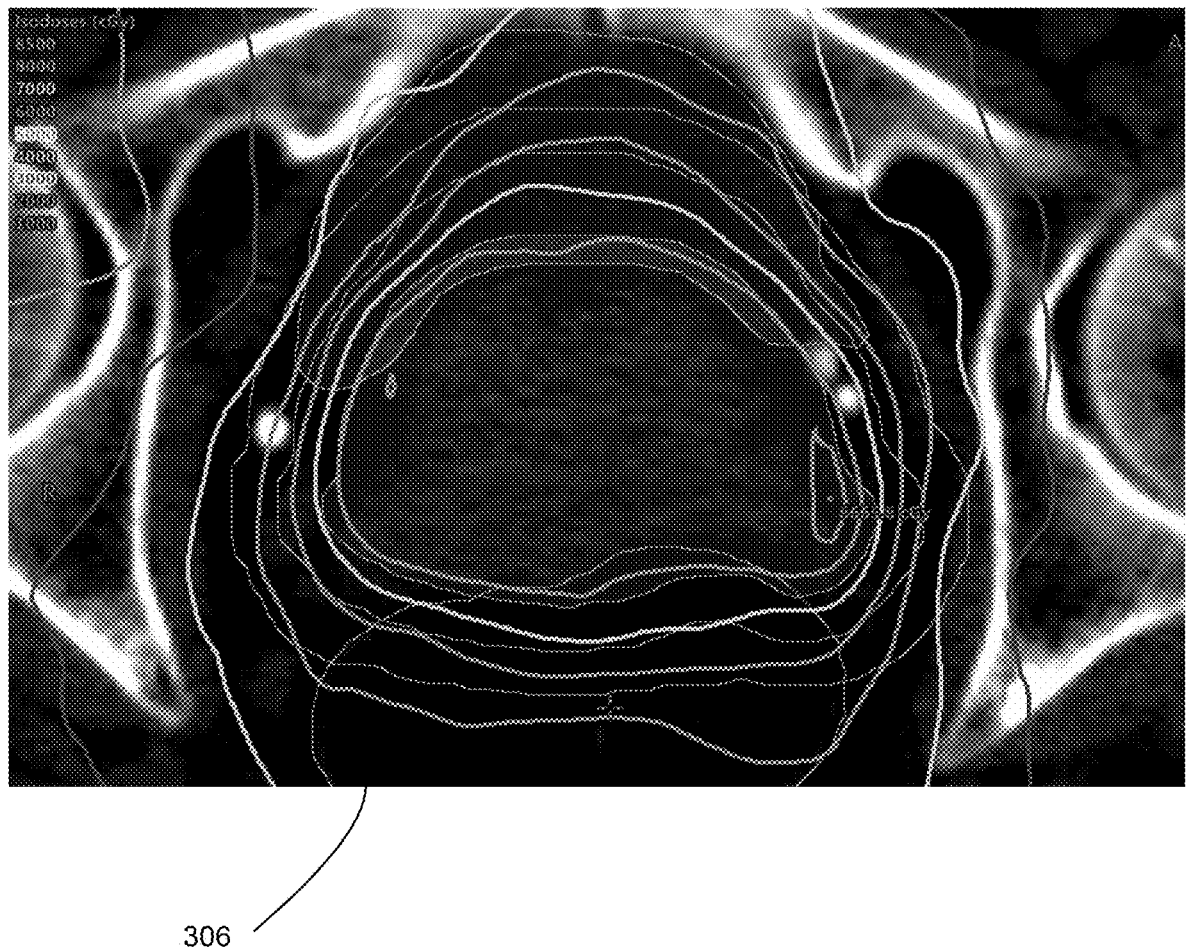
FIG. 3C is an illustration of another example of a voxel that share a range of boundary distances, forming a shell around the PTV in three planes of the patient, the illustration obtained by one or more elements consistent with the current subject matter.

FIG. 3 is an illustration of a set of voxels that share a range of boundary distances, forming a shell around the PTV in three planes of the patient, 302, 304 and 306. The range of boundary distances can be provided by $r_1 < r_{PTV} < r_2$ forming a shell around a PTV. This shell can be a structure with a differential DVH.

Figure 4:
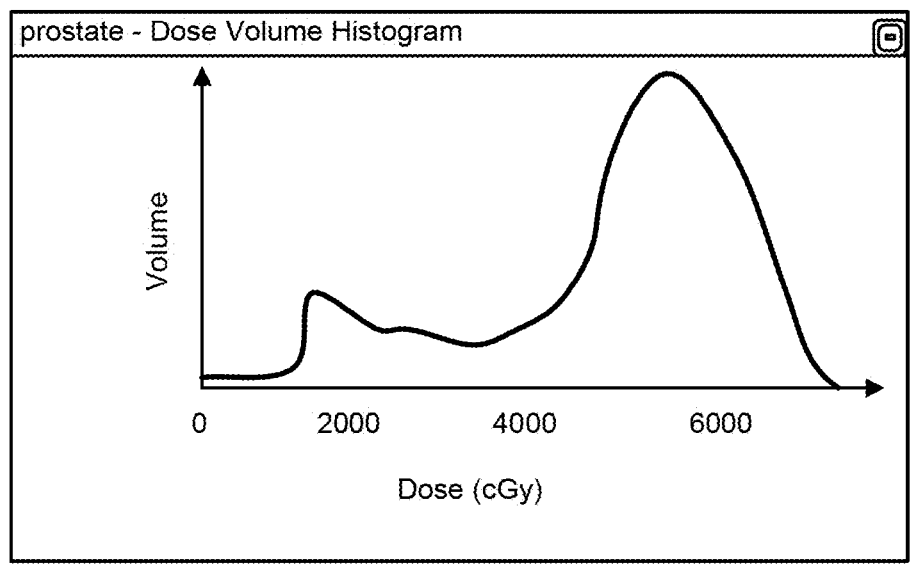
FIG. 4 is a graph summarizing the one-dimensional measured dose in the voxels in the range of boundary distances $r_1 < r_{PTV} < r_2$ forming a shell around PTV, for a given treatment plan, the graph generated by one or more elements consistent with the current subject matter.

FIG. 4 is a graph 400 summarizing the one-dimensional measured dose in the voxels in the range of boundary distances $r_1 < r_{PTV} < r_2$ forming a shell around PTV, for a given treatment plan.

Figure 5:
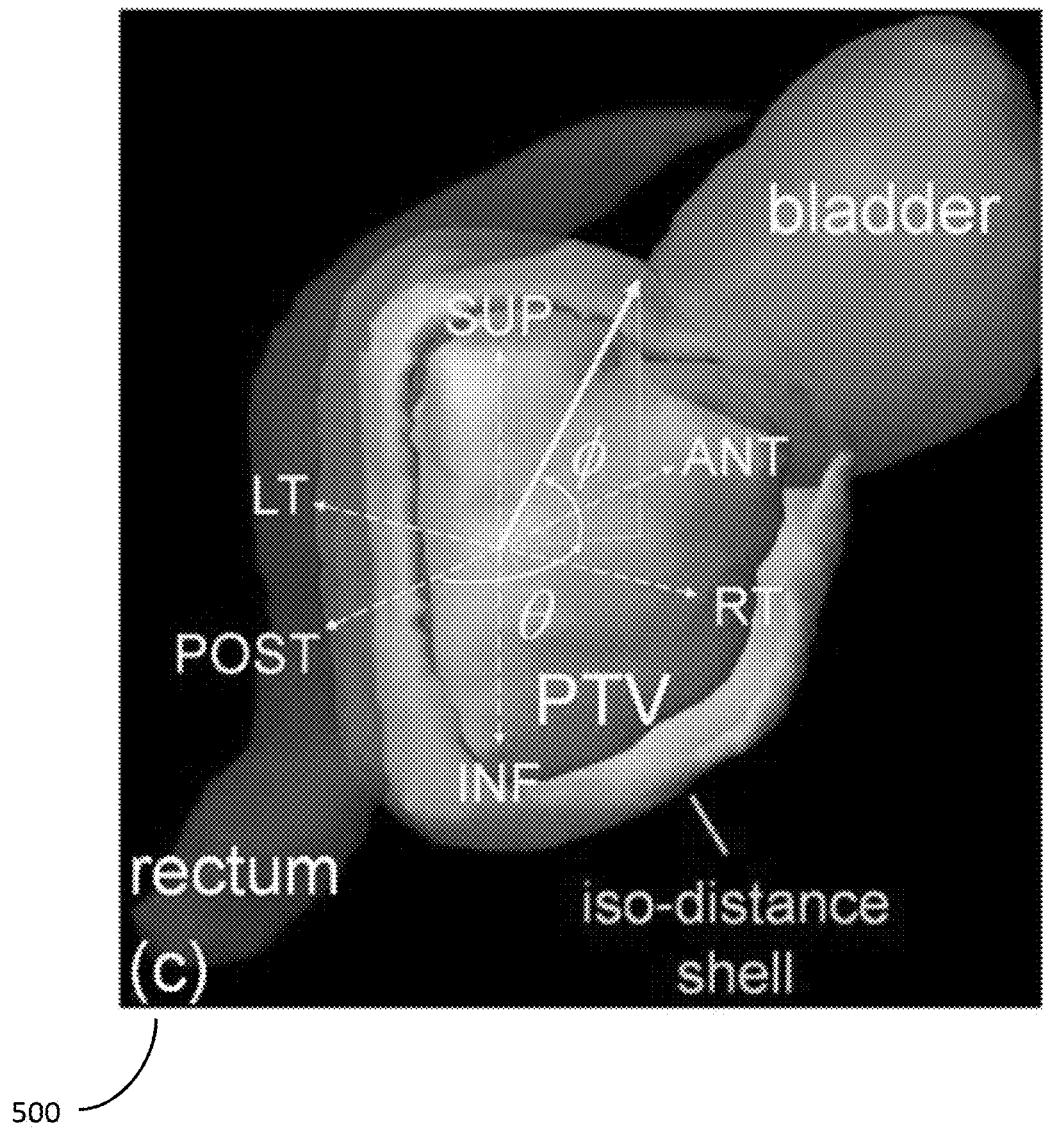
FIG. 5 is an illustration of a three-dimensional parameterization of the spatial location of individual voxels within a particular boundary distance shell according to a patient-centric coordinate system.
Figure 6:
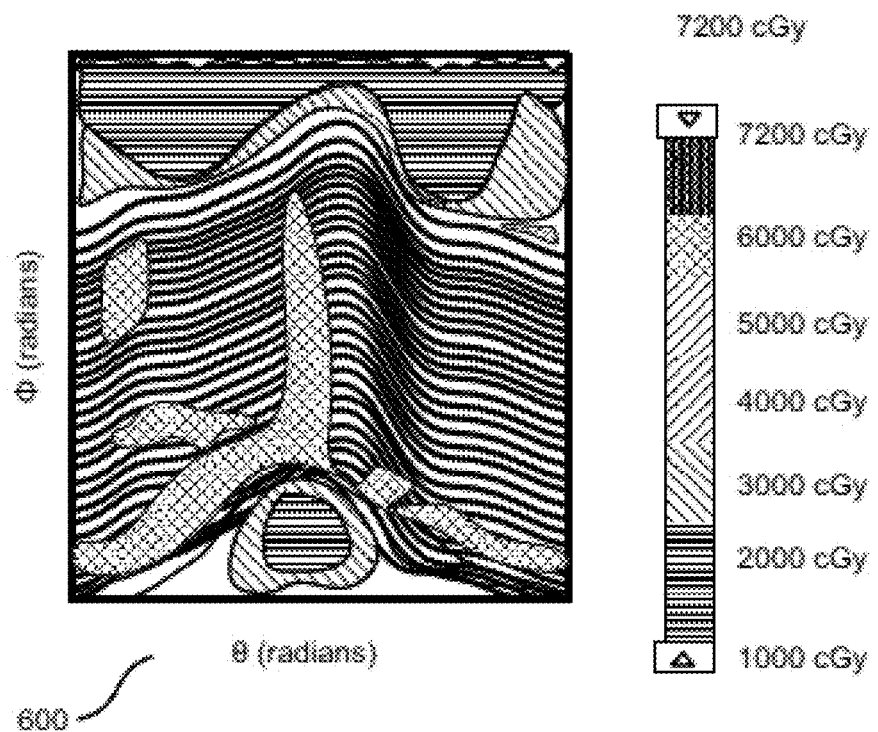
FIG. 6 is an illustration of a one-dimensional differential DVH determined based on the DVH prediction of FIG. 4.

FIG. 5 is an illustration 500 of a three-dimensional parameterization of the spatial location of individual voxels within a particular boundary distance shell according to a patient-centric coordinate system. A patient-centric coordinate system can include superior/inferior, anterior/posterior, and left/right components. The parameterization of the spatial location of individual voxels can be defined by azimuthal ($\theta$) and elevation ($\phi$) angles. The differential DVH of the boundary distance shell can thus be mapped to a 2D distribution, as shown in FIG. 6. FIG. 6 is an illustration 600 of a one-dimensional differential DVH determined based on the DVH prediction of FIG. 4. Three-dimensional dose prediction can include a determination of the two-dimensional dose pattern of FIG. 6, for all shells of the PTV, $r_{PTV}$.

The data corresponding to the spatial position of one or more volume elements of the patient can include the boundary distance $r_{OAR}$ of each volume element to each identified OAR.

In addition to the parameters listed on the preceding page, these contributed to the intrinsic voxel geometric parameters by computing the boundary distance $r_{OAR}$ to each OAR.

In some variations, the data corresponding to the spatial position of the one or more volume elements of a patient can be obtained from a commercial treatment planning system, or TPS. The information obtained from the TPS can include general information about the treatment such as patient information, the treatment setup, and the orientation of the treatment fields with respect to the patient. The information can include the outlines of the relevant patient anatomy, including the treatment target (PTV) and neighboring organs-at-risk (OARs).

In some variations, the spatial position of each dose voxel can be calculated with respect to organ structures. The minimum distance from the PTV boundary can be calculated for each voxel that lies outside the PTV. A matrix of voxel points with their spatial coordinates, distance from the PTV boundary, and observed dose can be stored in electronic storage memory for further operations.

At 204, data corresponding to a set-up of a radiation therapy delivery system for delivering one or more radiation fields to the patient can be received at the at least one data processor. In some variations, the data corresponding to a set-up of a radiation therapy delivery system can be received at the platform server 102.

The data corresponding to a set-up of a radiation therapy delivery system for delivering one or more radiation fields to the patient can include field angles, field strengths, field widths, or the like, of the fields delivered to the patient. The data corresponding to a set-up of a radiation therapy delivery system for delivering one or more radiation fields to the patient can include a position of the couch, gantry, or the like, with respect to one or more elements of the radiation therapy delivery system. The data corresponding to a set-up of a radiation therapy delivery system for delivering one or more radiation fields to the patient can include a position of the couch, gantry, or the like, with respect to one or more elements of the radiation therapy delivery system. The data corresponding to a set-up of a radiation therapy delivery system for delivering one or more radiation fields to the patient can include an orientation of the couch, gantry, or the like, with respect to one or more elements of the radiation therapy delivery system.

In some variations, the data corresponding to a set-up of a radiation therapy delivery system can include a dose matrix calculated by the TPS, representing the 3D spatial information of how much ionizing radiation is deposited at each point inside the patient.

In some variations, the system can make an accurate prediction for the dose file, including magnitude of radiation absorption for every point inside of a new patient.

Based on the data corresponding to the treatment setup (e.g., couch angle, gantry angles, field sizes, and the like) the number of fields (e.g., photon beams, or the like) that are seen by each voxel point in the patient can be calculated. In some variations, this calculation can be limited to the volume elements residing outside the PTV. In those variations, for the volume elements, or voxels, residing within the PTV, the distance from the PTV boundary can be calculated.

In some variations, the calculation to determine the number of fields seen by each voxel can be limited to the voxels residing within the PTV. Alternatively or additionally, the treatment of voxels residing within the PTV can be different to the treatment of the voxels residing outside the PTV. The determination of the amount and intensity of the radiation fields intersecting voxels within the PTV may be performed separately from the determination of the amount and intensity of the radiation fields intersecting voxels outside the PTV. Separate calculation of the two groups of voxels can introduce efficiencies into the generation of the three-dimensional radiation dose matrix for the patient.

At 206, the number of radiation fields delivered by the radiation therapy delivery system that will intersect with individual volume elements of the one or more volume elements of the patient, can be determined. In some variations, determining the number of radiation fields delivered by the radiation therapy delivery system that will intersect with individual volume elements of the one or more volume elements of the patient can be performed by radiation fields component 204. Determining, by the at least one data processor, the number of radiation fields delivered by the radiation therapy delivery system that will intersect with individual volume elements of the one or more volume elements of the patient can be limited to the one or more volume elements outside of the treatment target of the patient.

At 208, a three-dimensional radiation dose matrix for the patient can be generated. The three-dimensional radiation dose matrix can be determined based on a predictive model. The determining of the three-dimensional radiation dose matrix can be based on the number of radiation fields that will intersect with the one or more volume elements of the patient. In some variations, determining of the three-dimensional radiation dose matrix can be performed by radiation matrix component 106. Determining, by the at least one data processor, of the quality of radiation fields delivered by the radiation therapy delivery system that will intersect with individual volume elements of the one or more volume elements of the patient can be limited to the one or more volume elements outside of the treatment target of the patient.

In some variations, the three-dimensional radiation dose matrix can include the radiation exposure of the one or more volume elements of the patient. The radiation fields can include photon beams, ion beams, or the like.

Figure 7:
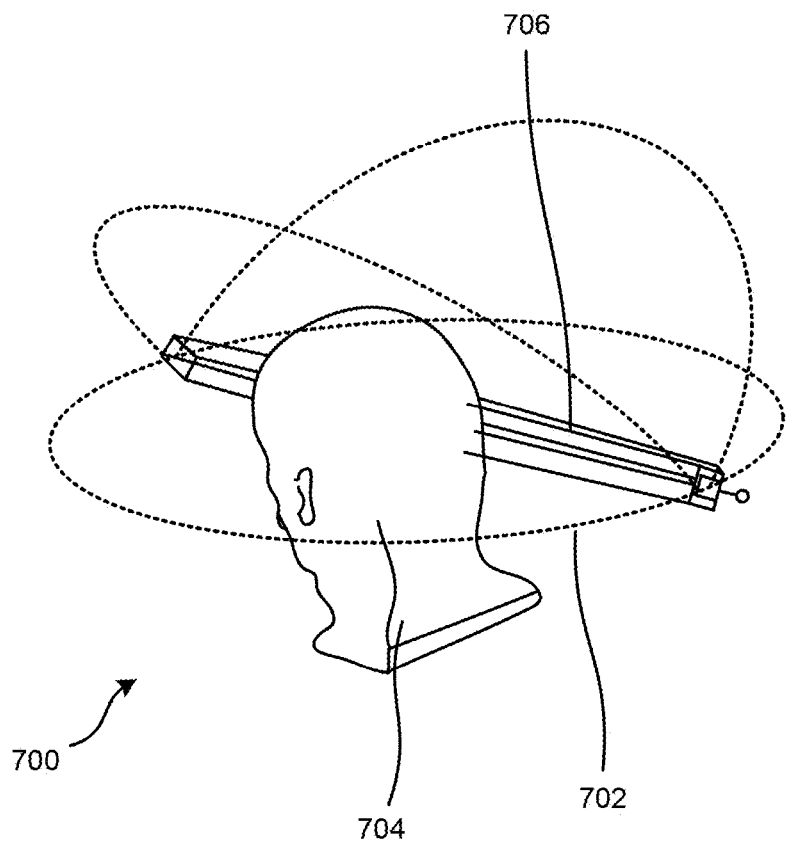
FIG. 7 is an illustration of field lines passing through a patient based on the position of a gantry of a radiation therapy delivery system.

The three-dimensional radiation dose matrix can determine the radiation exposure for volume elements within the patient based on the movement of an accelerator gantry with respect to the position of the patient, as sheen in FIG. 7. FIG. 7 is an illustration 700 of field lines 702 passing through a patient 704 based on the position of a gantry 706 of a radiation therapy delivery system.

In some variations the predictive model can be based on a plurality of reports that include observed radiation field patterns in one or more volume elements of prior patients. The plurality of reports can be stored, for example, in a voxel database, such as in electronic data storage 118. Predictive models rely on correlating the observed radiation energy deposition as it relates to the geometry of the individual patient anatomy, the corresponding geometry of the radiation field (e.g. photon beam, or the like), and the clinical goals for the patient's disease. The dose measured at a point in space can be correlated to the distance from the surface(s) of the PTV(s), the number of fields propagating through the point, and the orientation of the point with respect to the PTV(s).

A voxel database can be generated with all the input variables (e.g., volume of the PTV, distance from the PTV boundary, number of fields intersecting the voxel, directional orientation of voxel with respect to the PTV surface, principal component axes of the PTV volume, intersecting OAR, and the like). The database can include the target variable (e.g., observed dose, or the like) for a plurality of radiation therapy plans on a plurality of patients.

Figure 8:
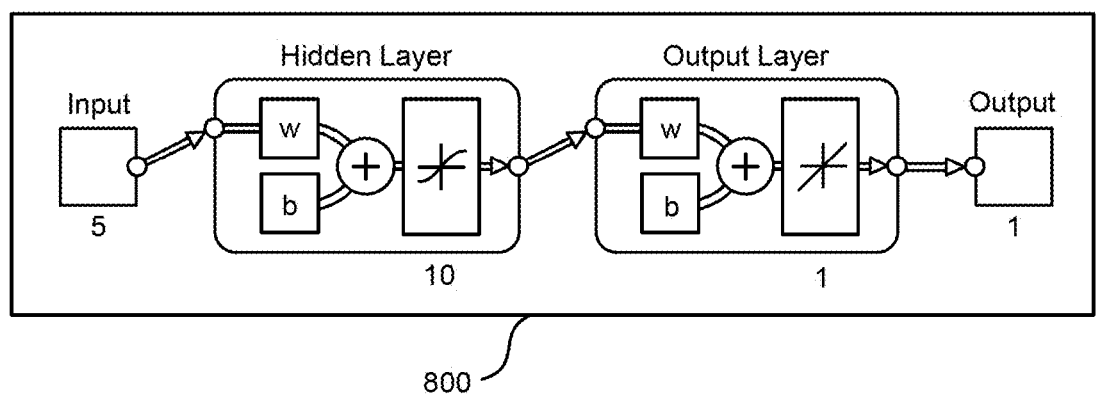
FIG. 8 is an illustration of a schematic of an artificial neural network (ANN) having one or more features consistent with the current subject matter.

In some variations the predictive model can be trained using a neural network, or other processor-based predictive techniques and circuits, neural network circuits, or the like. The predictive model can be configured to use historical patient data. The historical patient data can be stored on electronic storage devices, such as electronic storage device 118. In some variations, a neural network can be employed to perform one or more functions on the voxel database. An artificial neural network (ANN) function can be called to train the predictive model. FIG. 8 is an illustration of a schematic 800 of an ANN having one or more features consistent with the current subject matter. The ANN can train the predictive model using samples stored and maintained in in the voxel database.

The trained ANN can be designed to receive a new case as input. The new case can be represented by a structure set and beam orientation information. The trained ANN can be configured to output a three-dimensional dose matrix that represents the expectation for the absorbed dose for every voxel inside the patient. The clinical intent for a new case can be matched with the clinical intent of the cases stored in the voxel database.

Figure 9A:
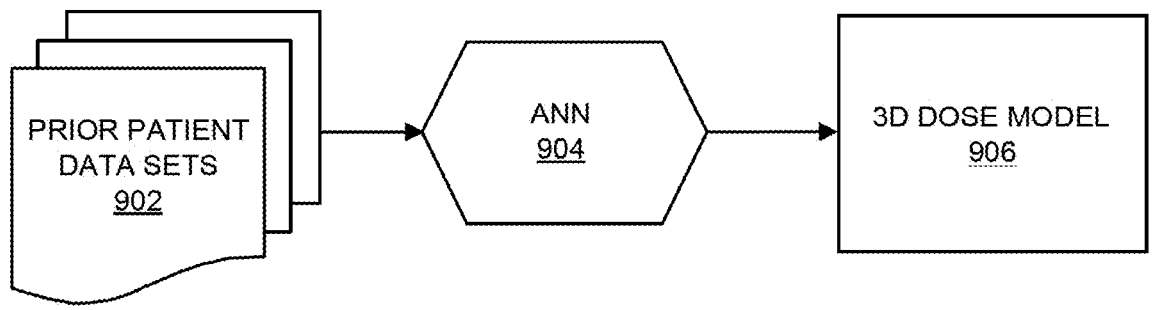
FIG. 9A is a diagram illustrating a process by which the ANN might be trained, in accordance with one or more features of the presently described subject matter.

FIG. 9A is a diagram 900 illustrating a process by which the ANN might be trained, in accordance with one or more features of the presently described subject matter. Patient data sets 902 are introduced into an ANN 904. The patient data sets 902 can include a structure set, three-dimensional imagery data, radiation field data, radiation dose data, or the like. The structure set can include information associated with individual volume elements, or voxels, as measured by three-dimensional imagery systems. Radiation field data can include a direction, size, strength, or the like of the radiation field to be administered to the patient. The radiation field data can include one or more attributes of the radiation therapy treatment equipment, such as whether the equipment include a collimator, or the ability to vary parts of the field during treatment, or the like. Radiation dose data can include a desired dose to be delivered to each of the identified volume elements within the patient. The patient data sets 902 can also include data associated with observed radiation at the volume elements of the patient.

Figure 10A:
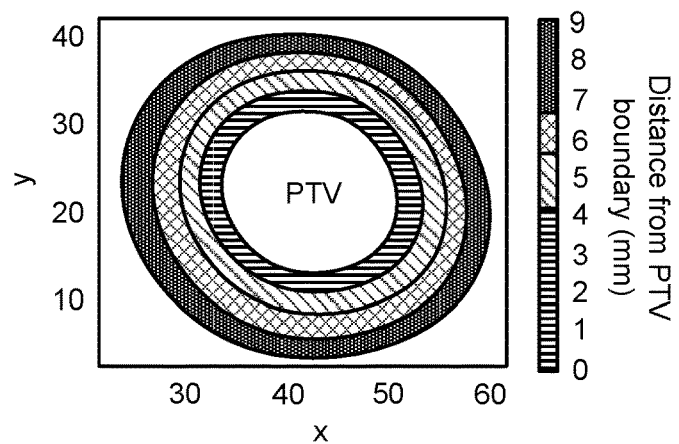
FIG. 10A shows the minimum distance from PTV boundary to each voxel outside the PTV for a fixed z position.
Figure 10B:
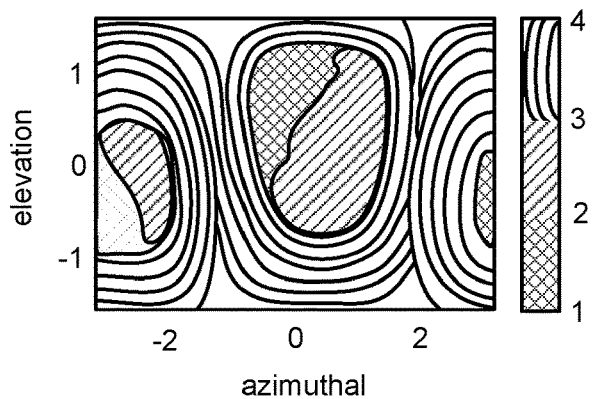
FIG. 10B shows the number of photon beams intersecting voxels located between 3-4.5 mm from the PTV boundary.

In some variations, training of the ANN 904 can be achieved by inputting data 902 corresponding to parameters of voxels within a defined distance from the boundary of the PTV. Inputs provided to the ANN can include intrinsic, (i.e. voxel-dependent) and extrinsic (i.e., case-dependent) parameters. Such parameters for individual voxels can include: PTV boundary distance $r_{PTV}$ (1 input), as shown in FIG. 10A which shows the minimum distance from PTV boundary to each voxel outside the PTV for a fixed z position; the number of intersecting fields (1 input), as shown in FIG. 10B which shows the number of photon beams intersecting voxels located between 3-4.5 mm from the PTV boundary; azimuthal & elevation angles θ, φ, (2 inputs); angles from PTV boundary (2 inputs); Cartesian coordinates x, y, z (3 inputs); OAR boundary distances $r_{OAR}$ (the number of inputs being case-dependent); PTV volume (1 input, extrinsic parameter); or the like.

Figure 10C:
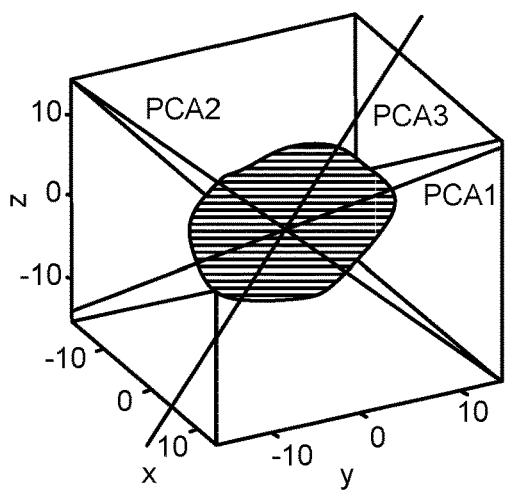
FIG. 10C shows PTV mass distribution in lab frame.

Ann's can correlate the geometric and plan parameters to the dose from a clinically approved plan for each voxel. Any parameters that could affect the dose distribution can be included in the training to improve the predictive ability. The geometrics of OARs and whole organ systems and anatomical regions. The distance to PTV ($r_{PTV}$) captures the general slope of dose gradient outside PTV with lower average dose as $r_{PTV}$ increases. PTV volume (VPTV) is known to influence dosimetric. The parameters can include number of beams ($N_{field}$) seen by each voxel. $N_{field}$ can be obtained from arc angles and can assume that each beam is conformal to the PTV. The azimuthal (Π) and elevation (θ) angles can be measured from the PTV centroid. Assuming a uniformly distributed mass, the principal component axis of the PTV can be calculated. The azimuthal (α) and elevation (β) angles in the principal coordinate system can also be used as inputs to train the ANN. FIG. 10C shows PTV mass distribution in lab frame. Other parameters, such as electron density taken from CT images, could be incorporated into the dose prediction.

Figure 9B:
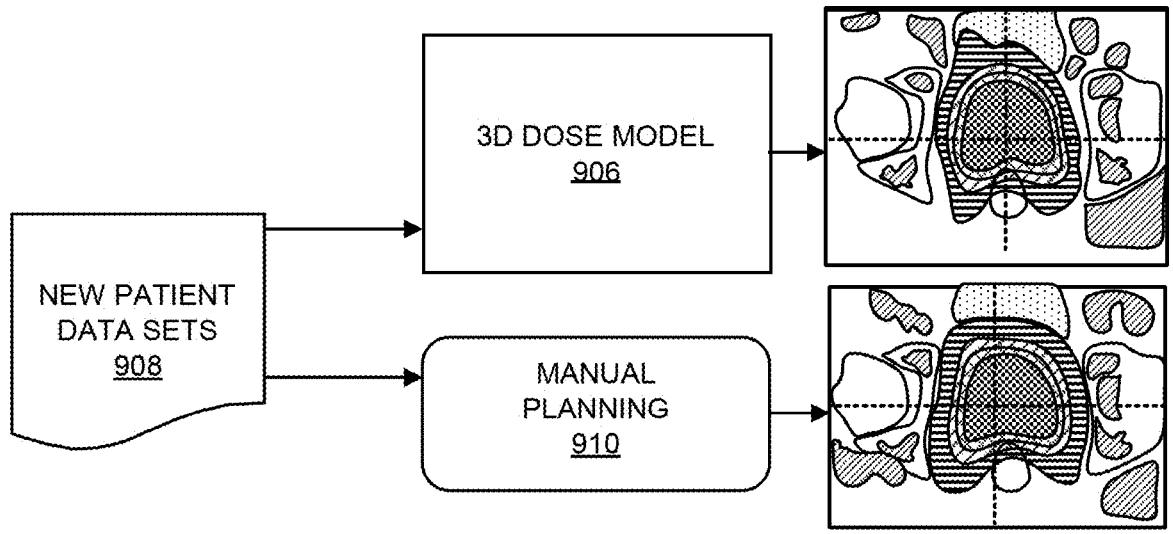
FIG. 9B is an illustration of schematic for generating a radiation dose prediction, according to one or more elements of the presently described subject matter.

FIG. 9B is an illustration of schematic for generating a radiation dose prediction, according to one or more elements of the presently described subject matter. New patient data sets 908 can be received by the system. The new patient data sets 908 can include information similar to the information included in the prior patient data sets 902. The 3D dose model 906, generated by the ANN 904 can operate on the new patient data sets 902 to facilitate the generation of a predicted three-dimensional dose matrix. Manual physician planning 910 can be used to generate a three-dimensional dose matrix. The manual physician planning 910 can augment the three-dimensional model 906 to provide a physician modified three-dimensional dose matrix.

In some variations, the analysis of the volume elements can be limited to those volume elements that receive above a threshold amount of radiation dose (DRx). Limiting the analysis to those volume elements that receive above a threshold amount of DRx can reduce the computational time to analyze the volume elements. The threshold DRx can be selected at a level where exposure to the threshold DRx will provide limited harm to the volume elements. An example of the threshold DRx can be 10% of the DRx.

Figure 11:
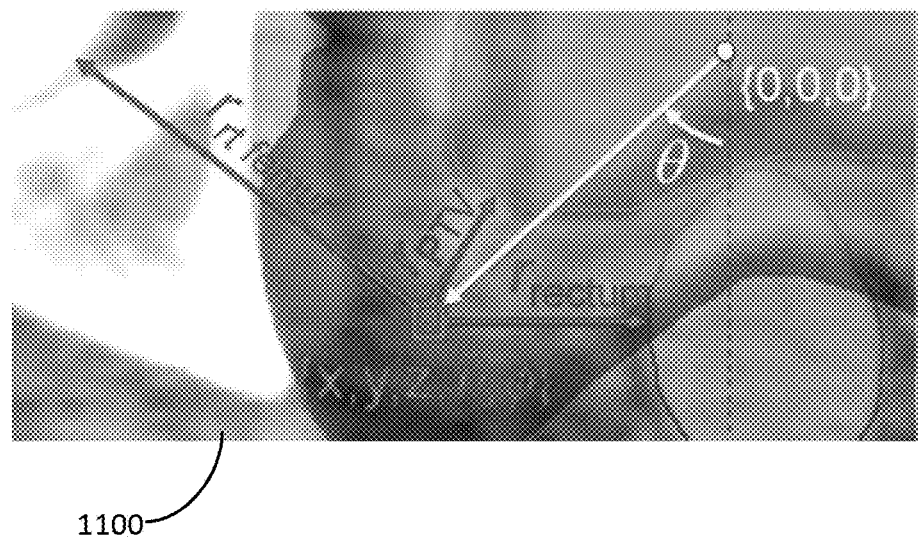
FIG. 11 is an illustration of a representation of $r_{PTV}$, $\theta$, x, y, z, and $r_{OAR}$ for an individual voxel.

FIG. 11 is an illustration of a representation 1100 of $r_{PTV}$, θ, x, y, z, and $r_{OAR}$ for an individual voxel. FIG. 11 illustrates a specific example of a PTV located in the prostate of a patient.

Figure 12A:
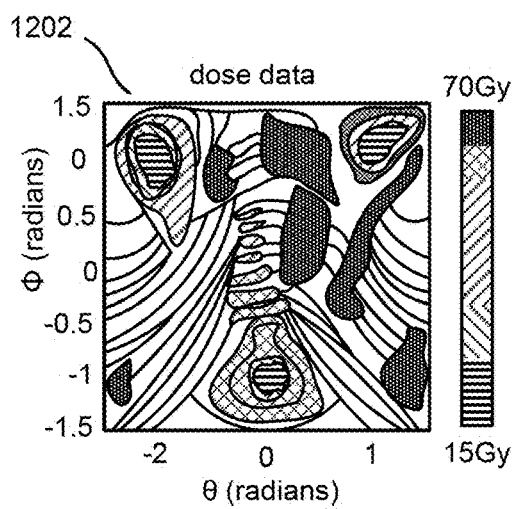
FIG. 12A shows an illustration of a single shell (6 mm $r_{PTV}$<9 mm) around the PTV illustrated in FIG. 11.
Figure 12B:
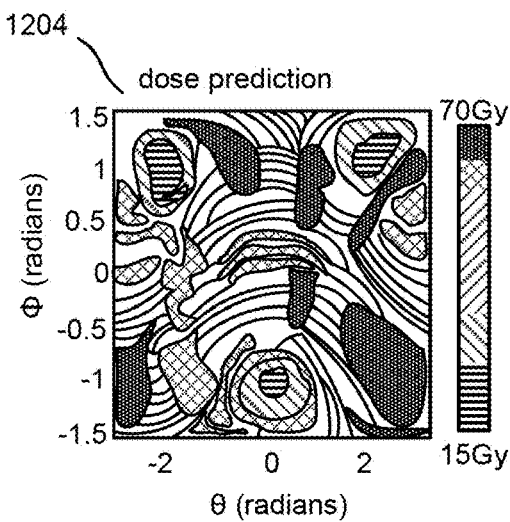
FIG. 12B shows an illustration of the three-dimensional prediction capturing the spatial features of the shell.
Figure 12C:
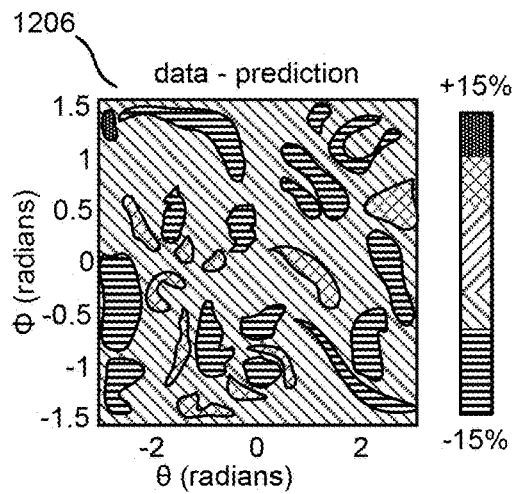
FIG. 12C shows an illustration of a dose difference map across the region.
Figure 12D:
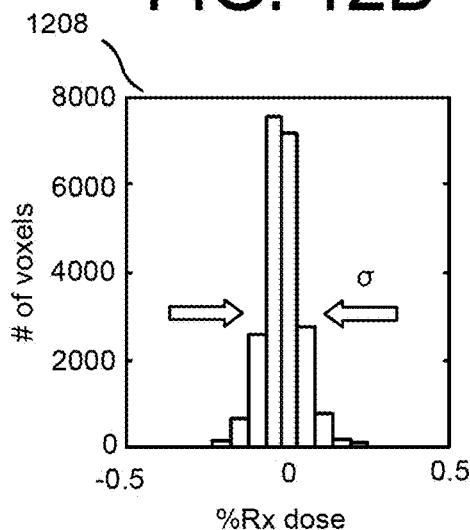
FIG. 12D shows an illustration of a histogram quantifying the accuracy of the prediction on a voxel-by-voxel basis.
Figure 12E:
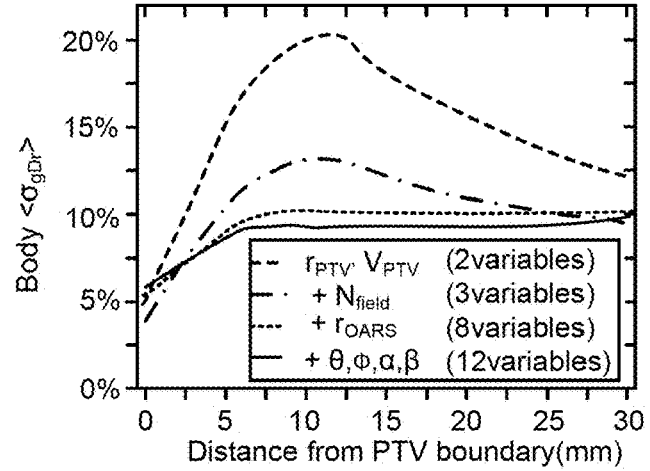
FIG. 12E shows a graph of the standard deviation ($\sigma$) of the dose differences as a function of $r_{PTV}$.

FIGS. 12A-12E are illustrations quantifying the accuracy of three-dimensional radiotherapy dose predictions, predicted by a system having one or more elements consistent with the presently described subject matter. FIG. 12A shows an illustration 1202 of a single shell (6 mm<$r_{PTV}$<9 mm) around the PTV illustrated in FIG. 11. FIG. 12B shows an illustration 1204 of the three-dimensional prediction capturing the spatial features of the shell. FIG. 12C shows an illustration 1206 of a dose difference map across the region. FIG. 12D shows an illustration 1208 of a histogram quantifying the accuracy of the prediction on a voxel-by-voxel basis. FIG. 12E shows a graph 1210 of the standard deviation (σ) of the dose differences as a function of $r_{PTV}$. As shown, the standard deviation, σ, decreases with incorporation of new geometric inputs, quantifying the predictive power of each geometric input provided by a system having one or more elements consistent with the presently described subject matter.

In some variations, the predictive model can be trained independently for different anatomical regions. For example, the predictive model can be trained by the ANN for prostate cancer, independently of intracranial cancers, independently of lung cancers, independently of spinal cancers, or the like. In other variations, the predictive model can use anatomical features of PTVs and OARs in one region of the body to determine a three-dimensional dose matrix for another part of the body based on similarities of various anatomical regions within a body.

A three-dimensional dose predictive system can receive a data corresponding to the spatial position of one or more volume elements of a patient and data corresponding to a set-up of a radiation delivery system, with properly identified PTVs and OARs, and can output a three-dimensional radiation dose matrix for the patient. The lowest curve of the graph shown in FIG. 9D shows the total prediction uncertainty for a single case as a function of $r_{PTV}$, resulting in 5-7% prediction accuracy floor from the range of 0-30 mm.

Figure 13A:
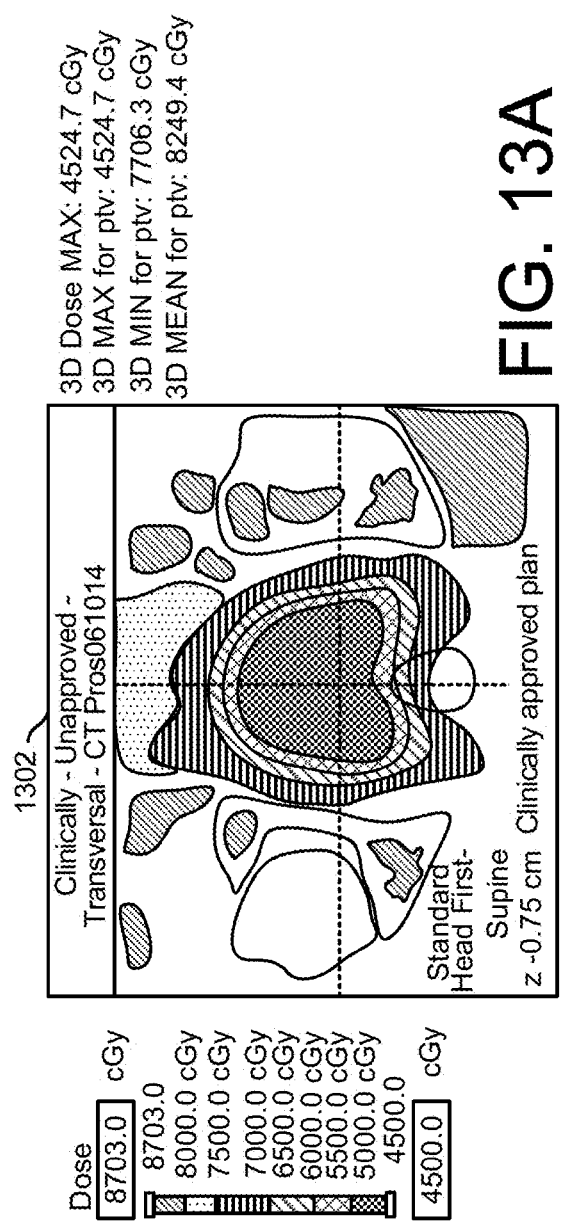
FIG. 13A shows a three-dimensional dose prediction determined manually for a patient with a brain tumor.
Figure 13B:
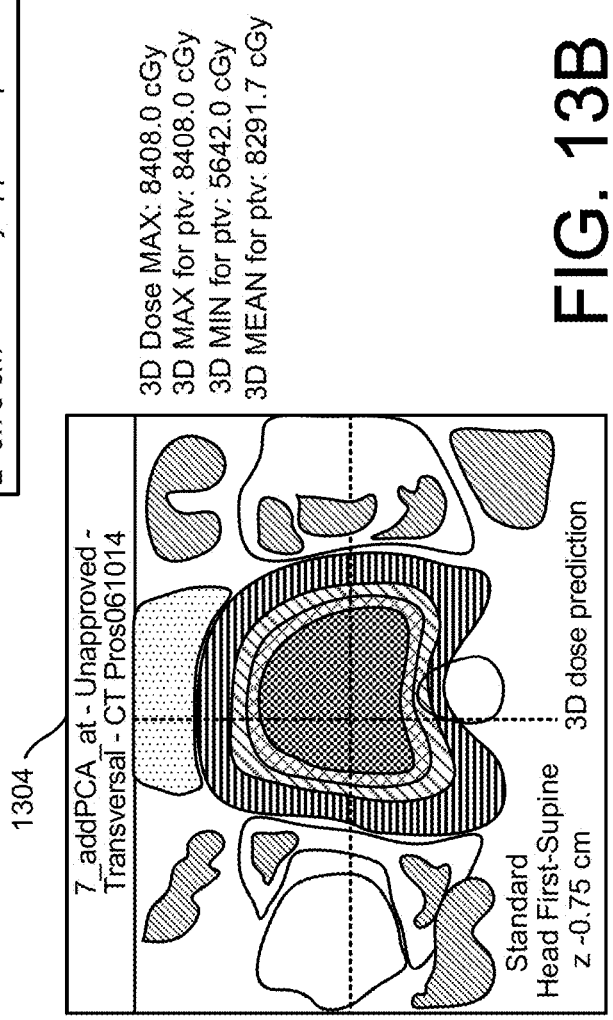
FIG. 13B shows a three-dimensional dose prediction for the area shown in FIG. 13A, determined using a system having one or more elements consistent with the current subject matter.
Figure 13C:
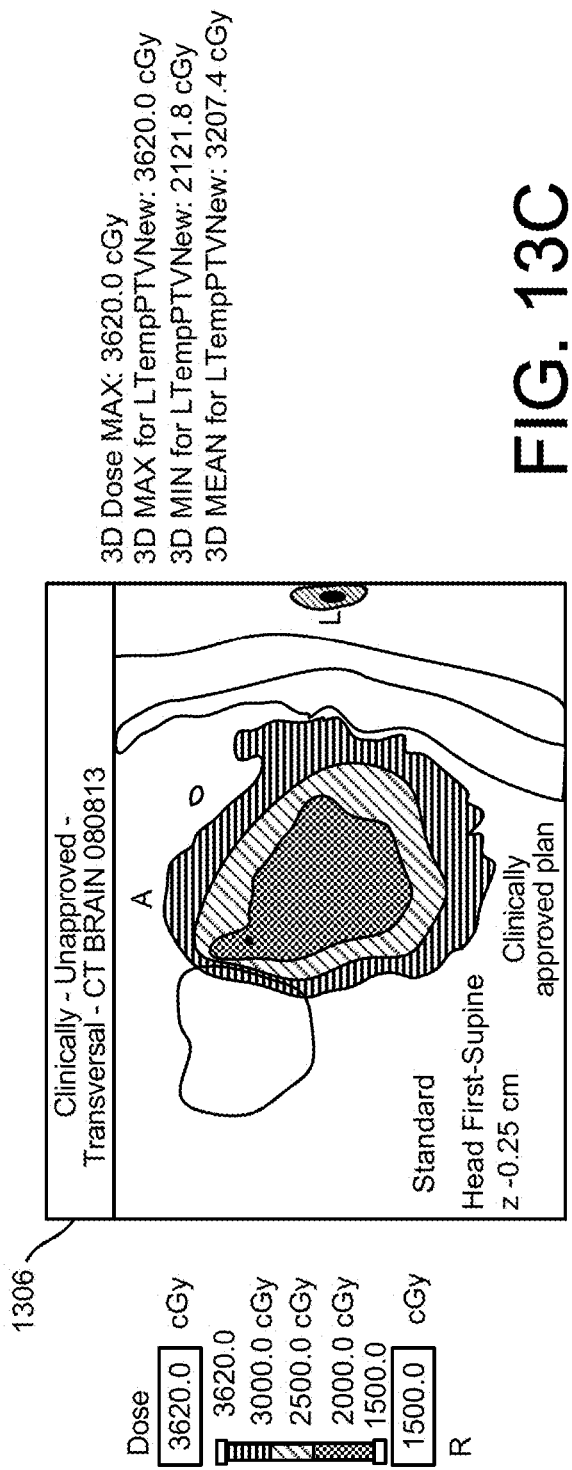
FIG. 13C shows a clinically-approved radiotherapy treatment plan.
Figure 13D:
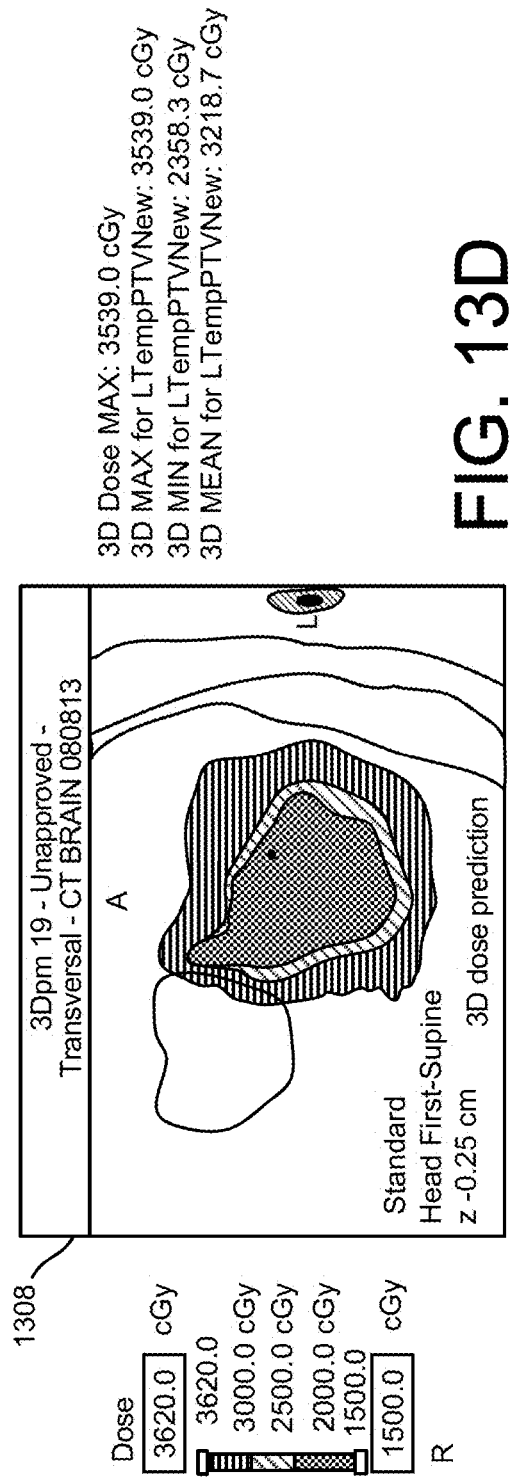
FIG. 13D shows a three-dimensional dose prediction determined using a system having one or more elements consistent with the current subject matter.

FIG. 13A shows a three-dimensional dose prediction 1302 determined manually for a patient with a brain tumor. FIG. 13B shows a three-dimensional dose prediction 1304 for the area shown in FIG. 13A, determined using a system having one or more elements consistent with the current subject matter. FIG. 13C shows a clinically approved radiotherapy treatment plan 1306. FIG. 13D shows a three-dimensional dose prediction 1308 determined using a system having one or more elements consistent with the current subject matter. The three-dimensional dose prediction shown in FIG. 13D shows the identified differential gradient regions at clinically relevant dose levels (e.g., >50% of 30Gy prescription). The primary OAR in FIGS. 13A-13D being the brainstem.

At 210 a radiation therapy treatment plan can be generated for the patient based on the three-dimensional radiation dose matrix for the patient. The radiation therapy treatment plan can be generated by the platform server 102. In some variations, the radiation therapy treatment plan can be generated by a user device, such as user device(s) 110. In some variations, the radiation therapy treatment plan can be generated by one or more computing systems associated with the radiation therapy treatment system 116. The treatment plan may be based on information provided or calculations performed by the platform server 102.

The radiotherapy treatment plan generated at 210, may be generated by performing one or more optimizations on an existing treatment plan, based on the three-dimensional radiation dose matrix generated at 208. In some variations, the radiation treatment plan generated by the subject matter described herein can include Volumetric Modulated Arc Therapy (VMAT) sequences. The VMAT sequences can be based on the determined voxel-wise knowledge-based predictions.

The presently described subject matter contemplates multiple ways to optimize the treatment plan based on the generated voxel-wise knowledge-based predictions. One such method includes introducing beam apertures into the VMAT sequence. An improved VMAT sequence plan can be generated for each stage of the treatment plan.

A generalized cost function for VMAT or IMRT optimization based on 3D dose prediction can be provided by:

$$f(D) = \Sigma_i \lambda(\vec{x}_i, D_{pred}(\vec{x}_i), \delta D_{pred}(\vec{x}_i))[D_i - D_{pred}(\vec{x}_i)]^2$$

where $x_i$ is the position of the $i^{th}$ voxel, $D_{pred}(x_i)$ is the predicted dose at $x_i$, $\delta D_{pred}$ is the prediction uncertainty at $x_i$, and $\lambda(x_i, D_{pred}(x_i), \delta D_{pred}(x_i))$ is a weighting term. This weighting term can be used in at least two ways: (i) to account for the uncertainty in the three-dimensional dose prediction; and/or (ii) to prioritize dose agreement in particular anatomic structures and/or particular dose levels over others.

In some variations, it may be desirable to require a higher level of agreement with the predicted dose when the three-dimensional dose prediction model has a lower level of uncertainty, and allow for a lower level of agreement if the model has a higher level of uncertainty. In some variations, it may be desirable to have the most important voxels, e.g., the high-dose voxels of a serial OAR, most closely matching the three-dimensional dose prediction values. The presently described subject matter permits the voxel-wise dose predictions be achievable in the treatment plan (in contrast with the idealized thresholds typically used in treatment plan optimization, such as prescription dose for targets and zero dose for OARs), making sensitivity to the weights, and the need for tuning, much less likely to be an issue.

Figure 14A:
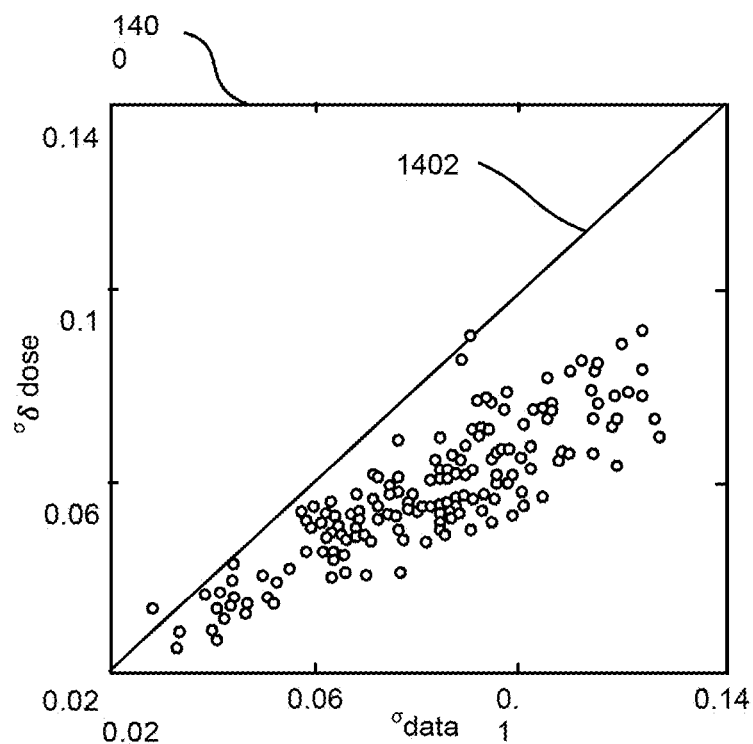
FIG. 14A is a graph showing reduced variation in three-dimensional dose prediction when using methods and systems having one or more elements consistent with the presently described subject matter.
Figure 14B:
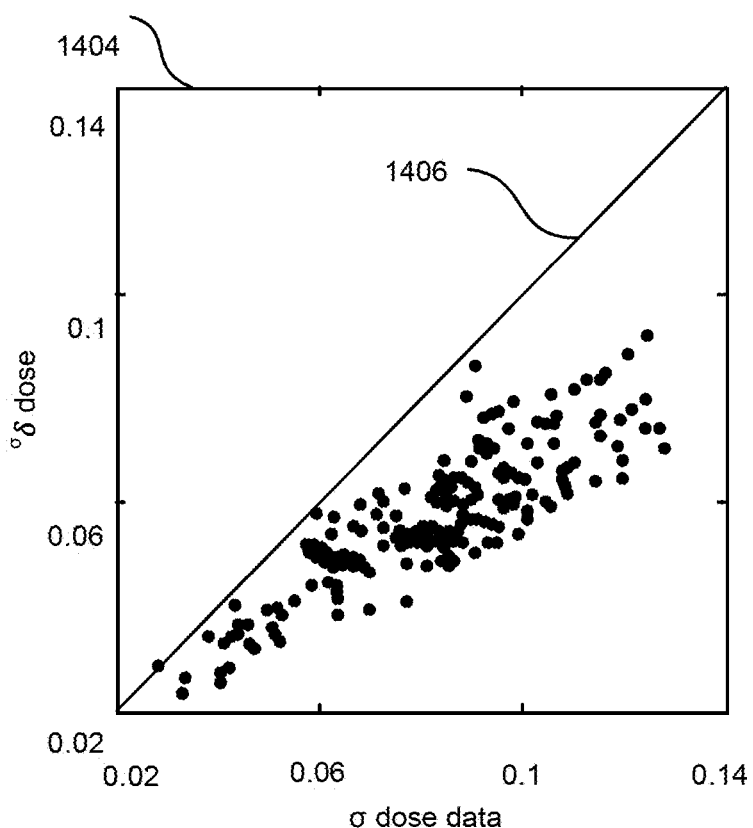
FIG. 14B is a graph showing standard deviations of observed data versus that of the dose difference (doses normalized to prescription dose); and, FIG. 15A depict examples of GUI consistent with the current subject matter.

FIG. 14A is a graph 1400 showing reduced variation in three-dimensional dose prediction when using methods and systems having one or more elements consistent with the presently described subject matter. Line 1402 represents the best possible three-dimensional dose prediction available using prior art DVH prediction methods. Data points below underneath this line represent three-dimensional dose predictions that give more accurate results at all distance intervals from the PTV. FIG. 14B is a graph 1404 showing standard deviations of observed data versus that of the dose difference (doses normalized to prescription dose). Line 1406 represents the best possible prediction with previous methods. Data points under this line represent improved three-dimensional dose prediction. FIG. 14B illustrates that the average residual error is nearly half that as achievable with previous methods.

A graphical user interface (GUI) can be generated for presentation on a screen of a user device associated with a medical practitioner. The GUI can be configured to display the generated radiation therapy treatment plan for the patient. Modifications to the generated radiation therapy treatment plan for the patient can be made via the GUI. Modifications may be analyzed the impact of the modifications can be determined for individual voxels. Notifications can be generated via the GUI to alert a medical practitioner of voxels, e.g. voxels of the OARs of the patient, put at risk by the modifications to the treatment plan.

A system, such as system 100, can be configured to facilitate a medical practitioner to reassign the status of particular OARs. In some variations this can be done on a voxel-by-voxel basis. In other variations, the status of OARs can be reassigned in-bulk. The association of each voxel with respect to OAR(s) can be known from at least the operations performed at 206. The medical practitioner, via the GUI, or otherwise, can reassign the status of the voxels associated with a particular OAR. For example, the status of an OAR can be converted to either the highest priority OAR (maximal dose avoidance) or as unspecified tissue (lowest dose avoidance priority).

The system can be further configured to facilitate "local" modification of the target coverage, increase the priority of hotspots by adjusting the voxel weighting term, or the like. As used herein, "local" modification can be performed by a medical practitioner involved in the treatment of the patient, as opposed to modification by the provider of such systems. In one exemplary variations, such local modifications can be configured to facilitate dragging of an isodose line presented through a GUI which can convert the movement of the isodose line to an associated adjustment of the underlying geometric parameters $X_{geo} \rightarrow X_{geo}' = X_{geo} + \delta X_{geo}$. This can be performed by generating an appropriate translation from the dragging of the isodose line on the GUI to the desired dose action in the treatment plan. Each isodose relocation can be converted to a reversible reassignment of surrounding voxel geometric properties. Voxels within a spherical neighborhood of a defined radius can be altered based on the isodose relocation. A desired dose alteration can define the range of the effect of the indicated isodose move.

The three-dimensional radiation dose matrix for the patient can be re-generated based on the modification to the isodose location. In the event that the radiation dose as predicted by the three-dimensional radiation dose matrix does not match that desired by the medical practitioner, the defined radius of the sphere can be iteratively modified to achieve the desired result. A radiation therapy treatment plan can, in turn, be regenerated based on the modified three-dimensional radiation dose matrix.

The presently described subject matter can provide medical practitioner control over the radiation therapy treatment plan and dose distribution, limited only by the delivery technique (e.g. VMAT) and the physical limitations of dose gradients with megavoltage photons.

FIG. 15 is a diagram of a GUI 1500 showing representations of the sequence of changes to the GUI based on input from a medical practitioner. GUI diagrams (c), (d) and (e) of FIG. 15 represent calculations performed by a computing system, such as platform server 102, user devices 110, devices associated with the radiation therapy treatment system 116, or the like. GUI diagrams (a), (b) and (f) of FIG. 15 represent GUIs that can be presented a physician that is modifying the generated radiotherapy treatment plan.

The particular set of GUI diagrams shown in FIG. 15 is for a case where a patient's clinical circumstances demand that the 50% line be excluded from the OAR, even at the expense of PTV coverage. At (a) a representation of a treatment plan is provided on a GUI. At (b) a physician selects the 50% isodose line (dotted arrow) and drags it to the desired location (solid arrow). At (c) this input via the GUI can be translated, for example by platform server 102, user device(s) 110, or the like, to a corresponding change in geometric parameters, until at (d) an appropriate $X_{geo} + \delta X_{geo}$ is found. At (e) the altered geometric parameters can result in a new predicted dose $D_{pred}'$, generated by one or more elements of the presently described subject matter. At (f) the GUI can be updated with a new deliverable dose distribution $D_{deliv}'$.

Without in any way limiting the scope, interpretation, or application of the claims appearing herein, a technical effect of one or more of the example embodiments disclosed herein may include the ability to predict three-dimensional dose distributions for the treatment planning process of a patient in need of radiation therapy, by not only providing information as to the effectiveness of a clinician's plans but also providing where inside the patient the dose distribution could be improved.

Without in any way limiting the scope, interpretation, or application of the claims appearing herein, a technical effect of one or more of the example embodiments disclosed herein may include the ability to provide treatment plans based on a volume-element-by-volume element optimization of the radiation distribution plan, eliminating unnecessary exposure of volume elements to radiation, and providing the ability to increase the radiation dose to the PTV.

Without in any way limiting the scope, interpretation, or application of the claims appearing herein, a technical effect of one or more of the example embodiments disclosed herein may include the ability to provide accurate three-dimensional dose predictions in the treatment planning process, even in response to significantly altered volume element modification, or tagging.

Without in any way limiting the scope, interpretation, or application of the claims appearing herein, a technical effect of one or more of the example embodiments disclosed herein may include providing predicted dose distribution that give clinicians a full picture of expected radiotherapy dose deposition that can be reviewed and evaluated just like a deliverable plan due to the retention of the spatial information. This can provide information so whether a plan can be improved and also where the plan should be improved.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method to be performed by at least one data processor forming at least part of a computing system, the method comprising:

selecting, by the at least one data processor, a first data corresponding to a spatial position of one or more volume elements of a patient;

selecting, by the at least one data processor, a second data corresponding to a set-up of a radiation therapy delivery system for delivering one or more radiation fields to the patient;

applying, by the at least one data processor, a predictive model to determine a quantity of radiation delivered by the radiation therapy delivery system having the set-up indicated by the second data to the one or more volume elements of the patient having the spatial position indicated by the first data, the predictive model determining the quantity of radiation delivered to the one or more volume elements by at least correlating a first geometry of the one or more volume elements and a second geometry of the one or more radiation fields to an observed radiation energy deposition; and generating, by the at least one data processor, a three-dimensional radiation dose matrix indicating the quantity of radiation delivered by the radiation therapy delivery system to the one or more volume elements of the patient.

2. The method of claim 1, wherein the quantity of radiation delivered by the radiation therapy delivery system is determined based on a quantity of the one or more radiation fields that intersect with the one or more volume elements of the patient.

3. The method of claim 2, further comprising:
determining, based at least on the three-dimensional radiation dose matrix, whether the one or more volume elements of the patient experiences a radiation dose exceeding a maximum radiation dose associated with each of the one or more volume elements.

4. The method of claim 1, wherein the first data includes the spatial position of the one or more volume elements with respect to a treatment target of the patient.

5. The method of claim 4, wherein the first data includes a distance of the one or more volume elements from the treatment target of the patient.

6. The method of claim 1, wherein the first data includes the spatial position of the one or more volume elements with respect to an anatomical structure of the patient.

7. The method of claim 1, wherein the first data includes a matrix of a plurality of volume elements in a vicinity of a treatment target of the patient.

8. The method of claim 1, wherein the second data includes one or more field angles of the one or more radiation fields.

9. The method claim 1, further comprising:
determining, by the at least one data processor, a quantity of the one or more radiation fields that will intersect with the one or more volume elements outside of a treatment target of the patient.

10. The method claim 1, further comprising:
determining, by the at least one data processor, a quantity of the one or more radiation fields that will intersect with the one or more volume elements within a treatment target of the patient.

11. A system comprising:
at least one data processor;
at least one memory coupled to the at least one data processor, the at least one memory storing instructions, which, when executed, cause the at least one data processor to perform operations comprising:
receiving a first data corresponding to a spatial position of one or more volume elements of a patient;
receiving a second data corresponding to a set-up of a radiation therapy delivery system for delivering one or more radiation fields to the patient;
applying a predictive model to determine a quantity of radiation delivered by the radiation therapy delivery system having the set-up indicated by the second data to the one or more volume elements of the patient having the spatial position indicated by the first data, the predictive model determining the quantity of radiation delivered to the one or more volume elements by at least correlating a first geometry of the one or more volume elements and a second geometry of the one or more radiation fields to an observed radiation energy deposition; and
generating a three-dimensional radiation dose matrix indicating the quantity of radiation delivered by the radiation therapy delivery system to the one or more volume elements of the patient.

12. The system of claim 11, wherein the quantity of radiation delivered by the radiation therapy delivery system is determined based on a quantity of the one or more radiation fields that intersect with the one or more volume elements of the patient.

13. The system of claim 12, wherein the at least one data processor is further caused to perform operations comprising:
determining, based at least on the three-dimensional radiation dose matrix, whether the one or more volume elements of the patient experiences a radiation dose exceeding a maximum radiation dose associated with each of the one or more volume elements.

14. The system of claim 11, wherein the first data includes the spatial position of the one or more volume elements with respect to a treatment target of the patient.

15. The system of claim 14, wherein the first data includes a distance of the one or more volume elements from the treatment target of the patient.

16. The system of claim 11, wherein the first data includes the spatial position of the one or more volume elements with respect to an anatomical structure of the patient.

17. The system of claim 11, wherein the first data includes a matrix of a plurality of volume elements in a vicinity of a treatment target of the patient.

18. The system of claim 11, wherein the second data includes one or more field angles of the one or more radiation fields for delivery to the patient.

19. The system claim 11, wherein the at least one data processor is further caused to perform operations comprising:
determining a quantity of the one or more radiation fields that will intersect with the one or more volume elements outside of a treatment target of the patient.

20. The system claim 11, wherein the at least one data processor is further caused to perform operations comprising:
determining, by the at least one data processor, a quantity of the one or more radiation fields that will intersect with the one or more volume elements within a treatment target of the patient.

21. The method of claim 1, wherein the predictive model determines the quantity of radiation delivered to the one or more volume elements by at least correlating a dose of radiation measured at a point in space, a distance from the point in space to a surface of the one or more volume elements, a quantity of radiation fields propagating through the point in space, and an orientation of the point in space relative to the one or more volume elements.

22. The method of claim 1, wherein the first data includes one or more of a field angle, a field strength, a field width, a couch position, or a gantry position.

* * * * *